US008839961B2

(12) United States Patent
Nishimi et al.

(10) Patent No.: US 8,839,961 B2
(45) Date of Patent: Sep. 23, 2014

(54) METHOD FOR PRODUCING A BIOSENSOR

(75) Inventors: Taisei Nishimi, Kanagawa (JP);
Toshihide Ezoe, Kanagawa (JP); Koji Kuruma, Kanagawa (JP); Masayuki Kawakami, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 811 days.

(21) Appl. No.: 11/604,260

(22) Filed: Nov. 27, 2006

(65) Prior Publication Data

US 2007/0258866 A1     Nov. 8, 2007

(30) Foreign Application Priority Data

| Nov. 25, 2005 | (JP) | ................................. | 2005-340104 |
| Nov. 25, 2005 | (JP) | ................................. | 2005-340105 |
| Feb. 22, 2006 | (JP) | ................................. | 2006-045616 |
| Feb. 22, 2006 | (JP) | ................................. | 2006-045617 |
| Sep. 15, 2006 | (JP) | ................................. | 2006-250383 |

(51) Int. Cl.

| B01J 14/00 | (2006.01) |
| C12Q 1/68 | (2006.01) |
| G01N 33/544 | (2006.01) |
| B01J 47/00 | (2006.01) |
| B01J 20/32 | (2006.01) |
| B01D 15/36 | (2006.01) |
| G01N 33/543 | (2006.01) |

(52) U.S. Cl.
CPC ............ *B01J 47/006* (2013.01); *B01J 20/3204* (2013.01); *B01J 20/3208* (2013.01); *B01J 20/3219* (2013.01); *B01J 20/3257* (2013.01); *B01J 20/3272* (2013.01); *B01J 20/3289* (2013.01); *B01J 20/3221* (2013.01); *B01D 15/361* (2013.01); *G01N 33/54393* (2013.01)

USPC ................ 210/500.27; 210/500.37; 427/243; 436/529; 435/4; 435/6

(58) Field of Classification Search
None
See application file for complete search history.

(56) References Cited

U.S. PATENT DOCUMENTS

| 3,804,631 A | 4/1974 | Faust |
| 3,930,865 A | 1/1976 | Faust et al. |
| 4,139,391 A | 2/1979 | Ikeda et al. |
| 4,537,855 A | 8/1985 | Ide |

(Continued)

FOREIGN PATENT DOCUMENTS

| EP | 1 696 235 A | 8/2006 |
| EP | 1 724 584 A | 11/2006 |

(Continued)

OTHER PUBLICATIONS

Wang et al. "Improved method for the preparation of carboxylic acid and amine terminated self-assembled monolayers of alkanethiolates". 2005. Langmuir. vol. 21, No. 7, pp. 2633-2636.*

(Continued)

*Primary Examiner* — Krishnan S Menon
(74) *Attorney, Agent, or Firm* — Sughrue Mion, PLLC

(57) ABSTRACT

An object of the present invention is to provide a biosensor comprising a hydrogel capable of immobilizing a physiologically active substance thereon, which can be produced conveniently by use of a safe material, and a method for producing the same. The present invention provides a method for producing a biosensor, which comprises bringing a polymer containing an activated carboxyl group into contact with a substrate surface coated with an organic layer having an amino group to thereby bind the polymer to the organic layer.

8 Claims, 7 Drawing Sheets

(56) References Cited

U.S. PATENT DOCUMENTS

| | | | |
|---|---|---|---|
| 4,600,687 | A | 7/1986 | Nakamura et al. |
| 4,647,528 | A | 3/1987 | Yamada et al. |
| 4,687,727 | A | 8/1987 | Toyama et al. |
| 5,164,589 | A | 11/1992 | Sjödin |
| 5,313,264 | A | 5/1994 | Ivarsson et al. |
| 5,753,518 | A | 5/1998 | Karlsson |
| 6,080,488 | A * | 6/2000 | Hostettler et al. ......... 428/423.3 |
| 6,177,523 | B1 * | 1/2001 | Reich et al. ................... 525/459 |
| 6,289,286 | B1 | 9/2001 | Andersson et al. |
| 6,468,657 | B1 * | 10/2002 | Hou et al. ..................... 428/403 |
| 6,472,224 | B1 | 10/2002 | Wischerhoff et al. |
| 6,577,396 | B1 | 6/2003 | Naya |
| 6,864,984 | B2 | 3/2005 | Naya et al. |
| 2002/0080358 | A1 | 6/2002 | Shimizu |
| 2004/0043508 | A1 | 3/2004 | Frutos et al. |
| 2004/0191815 | A1 | 9/2004 | Kyo et al. |
| 2005/0214815 | A1 * | 9/2005 | Boschetti et al. ................. 435/6 |
| 2006/0040410 | A1 | 2/2006 | Nishimi et al. |

FOREIGN PATENT DOCUMENTS

| | | |
|---|---|---|
| EP | 1 826 563 A1 | 8/2007 |
| GB | 152372 | 8/1978 |
| GB | 2 006 454 A | 5/1979 |
| JP | 06-167443 | 6/1994 |
| JP | 2006-58071 A | 3/2006 |
| JP | 2006-90781 A | 4/2006 |
| WO | WO 90/05303 A1 | 5/1990 |
| WO | 99/30160 A | 6/1999 |
| WO | 03/075012 A | 9/2003 |
| WO | 2005/017122 A | 2/2005 |

OTHER PUBLICATIONS

Noble, Karl-Ludwig. "Waterborne polyurethanes". 1997. Progress in Organic Coatings. vol. 32, pp. 131-136.*

Lahiri et al. "A strategy for the generation of surfaces presenting ligands for studies of binding based on an active ester as a common reactive intermediate: a surface plasmon resonance study." 1999. Anal. Chem. vol. 71, pp. 777-790.*

Bioacore Sensor Surface Handbook. Feb. 2005.*

Slaughter Gymama E et al: "Improving Neuron-TTO-Electrode Surface Attachment Via Alkanethiol Self-Assembly: An Alternating Current Impedance Study." Langmuir vol. 20, No. 17, 2004, pp. 7189-7200, XP-002431659.

Houseman B T et al: "The Role of Ligand Density in the Enzymatic Glycosylation of Carbohydrates Preented on Self-Assembled Monolayers of Alkanethiolates on Gold". Angew Chem. Int. Ed, 1999.38, No. 6, Wiley-Vch Verlag, Weinheim, De, 1999, pp. 782-785, XP-002229682.

Metallo et al:"Using Bifunctional Polymers Presenting Vancomycin and Fluorescein Groups to Direct Anti-Fluorescein Antibodies to Self-Assembled Monolayers Presenting D-Alanine-D-Alanine Groups". 2003 American Chemical Society, vol. 125, No. 15, pp. 4534-4540, XP-002353047.

Revzin et al: "Fabrication of Poly(Ethylene Glycol) Hydrogel Microstructures Using Photolithography". Langmuir, vol. 17, No. 18, 2001, pp. 5440-5447, XP-009076111.

Freudenberg et al: "Covalent Immobilization of Cellulse Layers Onto Maleic Anhydride Copolymer Thin Films". Biomacromolecules, vol. 6, No. 3, 2005, pp. 1628-1634, XP-002373978.

Stefan Löfås et al., "A Novel Hydrogel Matrix on Gold Surfaces Plasmon Resonance Sensors for Fast and Efficient Covalent Immobilization of Ligands", J. Chem. Soc., Chem. Commun., 1990, pp. 1526-1529.

Esa Stenberg et al., "Quantitative Determination of Surface Concentration of Protein with Surface Plasmon Resonance Using Radiolabeled Proteins", Journal of Colloid and Interface Science, vol. 143, No. 2, May 1991, pp. 513-526.

Shigeki Kiyonaka et al., "Semi-wet peptide/protein array using supramolecular hydrogel", nature materials, vol. 3, Jan. 2004/, pp. 58-64/www.nature.com/naturematerials.

Dariusz Witt et al., "Applications, Properties and Synthesis of —Functionalized N-Alkanethiols and Disulfides—the Building Blocks of Self-Assembled Monolayers", Current Organic Chemistry, 2004, vol. 8, No. 15, 000-000.

J. Christopher Love et al., "Self-Assembled Monolayers of Thiolates on Metals as a Form of Nanotechnology", Chem. Rev., 2005, vol. 105, pp. 1103-1169.

R. Erik Holmlin et al., "Zwitterionic SAMs that Resist Nonspecific Adsorption of Protein from Aqueous Buffer", Langmuir 2001, vol. 17, pp. 2841-2850.

Emanuelel Ostuni et al., "Self-Assembled Monolayers That Resist the Adsorption of Proteins and the Adhesion of Bacterial and mammalian Cells", Langmuir, 2001, vol. 17, pp. 6336-6343.

Emanuele Ostuni et al., "A Survey of Structure—Property Relationships of Surfaces that Resist the Adsorption of Protein", Langmuir, 2001, vol. 17, pp. 5605-5620.

An Extended European Search Report dated May 9, 2008.

Office Action dated Mar. 3, 2011 in European Patent Application No. 06 024 402.7.

Office Action dated May 11, 2012 in European Patent Application No. 08 004 163.5.

Office Action dated May 11, 2012 in European Patent Application No. 06 024 402.7.

Office Action dated Feb. 25, 2013 in European Application No. EP 08 004 163.5.

Office Action issued in counterpart European Patent Application No. 08004163.5, dated Jun. 3, 2014.

* cited by examiner

METHOD FOR PRODUCING A BIOSENSOR

TECHNICAL FIELD

The present invention relates to a method for producing a biosensor and to a method for analyzing the interaction between biomolecules by use of the biosensor. Particularly, the present invention relates to a method for producing a biosensor for use in a surface plasmon resonance biosensor, and to a method for analyzing the interaction between biomolecules by use of the biosensor.

BACKGROUND ART

Recently, a large number of measurements using intermolecular interactions such as immune responses are being carried out in clinical tests, etc. However, since conventional methods require complicated operations or labeling substances, several techniques are used that are capable of detecting the change in the binding amount of a test substance with high sensitivity without using such labeling substances. Examples of such a technique may include a surface plasmon resonance (SPR) measurement technique, a quartz crystal microbalance (QCM) measurement technique, and a measurement technique of using functional surfaces ranging from gold colloid particles to ultra-fine particles. The SPR measurement technique is a method of measuring changes in the refractive index near an organic functional film attached to the metal film of a chip by measuring a peak shift in the wavelength of reflected light, or changes in amounts of reflected light in a certain wavelength, so as to detect adsorption and desorption occurring near the surface. The QCM measurement technique is a technique of detecting adsorbed or desorbed mass at the ng level, using a change in frequency of a crystal due to adsorption or desorption of a substance on gold electrodes of a quartz crystal (device). In addition, the ultra-fine particle surface (nm level) of gold is functionalized, and physiologically active substances are immobilized thereon. Thus, a reaction to recognize specificity among physiologically active substances is carried out, thereby detecting a substance associated with a living organism from sedimentation of gold fine particles or sequences.

In all of the above-described techniques, the surface where a physiologically active substance is immobilized is important. Surface plasmon resonance (SPR), which is most commonly used in this technical field, will be described below as an example.

A commonly used measurement chip comprises a transparent substrate (e.g., glass), an evaporated metal film, and a thin film having thereon a functional group capable of immobilizing a physiologically active substance. The measurement chip immobilizes the physiologically active substance on the metal surface via the functional group. A specific binding reaction between the physiological active substance and a test substance is measured, so as to analyze an interaction between biomolecules.

A method for producing a hydrogel has been disclosed in detail in, for example, JP Patent No. 2815120, as a detection surface having a functional group capable of immobilizing a physiologically active substance thereon. Specifically, a layer of 16-mercaptohexadecanol is bound to a gold film to thereby form a barrier layer. On this gold film, hydroxyl groups on the barrier layer are treated with epichlorohydrin and thereby epoxy-activated. In a subsequent step, dextran is attached to the barrier layer via ether linkages. The dextran matrix is next reacted with bromoacetic acid to thereby introduce carboxymethyl groups therein.

The following approach has been disclosed as an approach for immobilizing a physiologically active substance (e.g., a protein or amino acid) having an amino group into the carboxymethyl-modified dextran surface produced based on this procedure: a part of the carboxyl groups in the carboxymethyl-modified dextran are modified so as to give reactive ester function, for example, by treatment with an aqueous solution of N-hydroxysuccinimide (NHS) and N-(3-dimethylaminopropyl)-N'-ethylcarbodiimide (EDC) hydrochloride. The residual charges, that is, unreacted carboxyl groups, will contribute to effecting the concentration of the physiologically active substance on the detection surface. Such a detection surface can be brought into contact with an aqueous solution of the physiologically active substance (protein or amino acid) containing an amino group to thereby covalently bond the physiologically active substance containing an amino group to the dextran matrix.

The hydrogel produced by the aforementioned method is capable of three-dimensionally immobilizing the physiologically active substance containing an amino group, and therefore exhibits excellent performance as a detection surface of a biosensor. However, the method for producing a hydrogel using the procedures described above is complicated and requires long production time and the use of compounds such as epichlorohydrin and bromoacetic acid. Therefore, it presented a safety problem.

DISCLOSURE OF INVENTION

It is an object of the present invention to solve the aforementioned problem. Specifically, an object of the present invention is to provide a biosensor comprising a hydrogel capable of immobilizing a physiologically active substance thereon, which can be produced conveniently by use of a safe material, and a method for producing the same. A further object of the present invention is to provide a biosensor with a large amount of immobilization of a physiologically active substance and a small amount of nonspecific adsorption, and a method for producing the same.

The present inventors have conducted diligent studies for attaining the objects and consequently found that a hydrogel capable of immobilizing a physiologically active substance thereon can be produced conveniently by reacting a hydrophilic polymer having a carboxyl group in an active esterified state with a substrate having an amino group. Further, the present inventors have found that a hydrogel capable of immobilizing a physiologically active substance thereon can be produced conveniently by coating a substrate surface with an organic layer having a functional group and then reacting a hydrophilic polymer having a reactive group capable of reacting with the functional group in a thin film state with the substrate surface. The present invention has been completed base on these findings.

Thus, the first aspect of the present invention provides a method for producing a biosensor, which comprises bringing a polymer containing an activated carboxyl group into contact with a substrate surface coated with an organic layer having an amino group to thereby bind the polymer to the organic layer.

Preferably, the polymer containing an activated carboxyl group is a polymer containing an active esterified carboxyl group.

Preferably, the substrate is a metal surface or metal film.

Preferably, the metal is any of gold, silver, copper, platinum, and aluminum.

Preferably, the substrate surface coated with an organic layer having an amino group is a substrate surface coated with alkanethiol having an amino group.

Preferably, the alkanethiol having an amino group is either a compound comprising a thiol group and an amino group linked via an alkyl chain or a compound obtained by reaction between alkanethiol having a carboxyl group at the end and hydrazide or diamine.

Preferably, the substrate surface coated with an organic layer having an amino group is a substrate surface coated with a mixture of alkanethiol having an amino group and alkanethiol having a hydrophilic group.

Preferably, the hydrophilic group in the alkanethiol having a hydrophilic group is a hydroxyl group or oligoethylene glycol group.

Preferably, the mixture of alkanethiol having an amino group and alkanethiol having a hydrophilic group comprises the alkanethiol having an amino group and the alkanethiol having a hydrophilic group at a molar ratio ranging from 1/1 to 1/1,000,000.

Preferably, the alkanethiol having an amino group has a molecular length larger than that of the alkanethiol having a hydrophilic group.

Preferably, the polymer containing a carboxyl group is polysaccharide.

Preferably, the polymer containing a carboxyl group has an average molecular weight of 1,000 to 5,000,000.

Preferably, the polymer containing an activated carboxyl group is reacted in the state of a thin film formed on the substrate with the organic layer having an amino group.

Preferably, the thin film is formed on the substrate by a spin coating method or spray coating method.

Preferably, the polymer containing an activated carboxyl group is a polymer which is obtained by activating a polymer containing a carboxyl group with a carbodiimide derivative, a nitrogen-containing compound or a phenol derivative.

Preferably, the carbodiimide derivative is water-soluble.

Preferably, the carbodiimide derivative is any of the compounds 1 to 3.

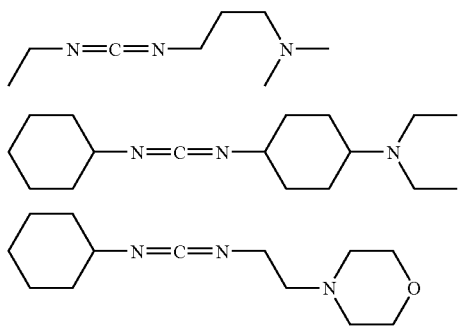

Preferably, the nitrogen-containing compound is a compound of the following formula (Ia) or (Ib):

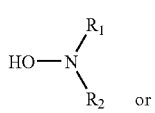

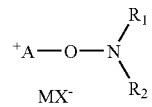

wherein $R_1$ and $R_2$ each independently represents a carbonyl group, a carbon atom or a nitrogen atom, which may have a substituent, or $R_1$ and $R_2$ may be bound to form a 5- or 6-membered ring, A represents a carbon atom or a phosphorus atom, which has a substituent, M represents an (n–1) valent element, and X represents a halogen atom.

Preferably, the nitrogen-containing compound is a compound of the following formula (II):

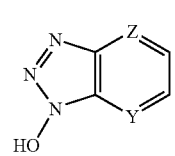

wherein X and Z each independently represents CH or a nitrogen atom.

Preferably, the phenol derivative is a compound having an electron-withdrawing group.

Preferably, the σ value of the electron-withdrawing group of the phenol derivative is 0.3 or more.

Preferably, when the polymer containing a carboxyl group is active-esterified, a carbodiimide derivative is used in combination with a nitrogen-containing compound, or a carbodiimide derivative is used in combination with a phenol derivative.

Preferably, when the polymer containing a carboxyl group is activated, the following morpholine derivative is used.

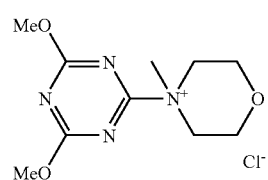

Preferably, the molar ratio of the carbodiimide derivative or the morpholine derivative with respect to the carboxyl group in the polymer is $1 \times 10^{-4}$ to 1.

Preferably, the molar ratio of the nitrogen-containing compound with respect to the carboxyl group in the polymer is $1 \times 10^{-7}$ to 1.

The second aspect of the present invention provides a method for producing a biosensor, which comprises a step of bringing, into contact with a substrate surface coated with an organic layer having a functional group, a hydrophilic polymer having a reactive group capable of reacting with the functional group to thereby bind the hydrophilic polymer to the organic layer, wherein the hydrophilic polymer having a reactive group in a thin film state is brought into contact with the substrate surface.

Preferably, the substrate is a metal surface or metal film.

Preferably, the metal is any of gold, silver, copper, platinum, and aluminum.

Preferably, the substrate surface coated with an organic layer having a functional group is a substrate surface coated with alkanethiol having a functional group.

Preferably, the substrate surface coated with an organic layer having a functional group is a substrate surface coated with alkanethiol having an amino group.

Preferably, the alkanethiol having an amino group is either a compound comprising a thiol group and an amino group linked via an alkyl chain or a compound obtained by reaction between alkanethiol having a carboxyl group at the end and hydrazide or diamine.

Preferably, the substrate surface coated with an organic layer having a functional group is a substrate surface coated with a mixture of alkanethiol having an amino group and alkanethiol having a hydrophilic group.

Preferably, the hydrophilic group in the alkanethiol having a hydrophilic group is a hydroxyl group or oligoethylene glycol group.

Preferably, the mixture of alkanethiol having an amino group and alkanethiol having a hydrophilic group comprises the alkanethiol having an amino group and the alkanethiol having a hydrophilic group at a molar ratio ranging from 1/1 to 1/1,000,000.

Preferably, the alkanethiol having an amino group has a molecular length larger than that of the alkanethiol having a hydrophilic group.

Preferably, the reactive group in the hydrophilic polymer is a vinylsulfone group or precursor thereof, dichlorotriazine group, acetoacetyl group, or carboxylic acid active ester group.

Preferably, the hydrophilic polymer having a reactive group is polysaccharide.

Preferably, the hydrophilic polymer having a reactive group in a thin film state is brought into contact with the substrate surface by a spin coating method or spray coating method.

Another aspect of the present invention provides a biosensor which is produced by the method according to the present invention as mentioned above.

Preferably, the biosensor according to the present invention is used in nonelectrochemical detection, and is more preferably used in surface plasmon resonance analysis.

Further another aspect of the present invention provides a method for immobilizing a physiologically active substance onto a biosensor, which comprises a step of bringing the biosensor according to the present invention into contact with a physiologically active substance to thereby bind the physiologically active substance to the biosensor.

Further another aspect of the present invention provides a method for detecting or measuring a substance interacting with a physiologically active substance, which comprises a step of bringing a biosensor according to the present invention having a surface covalently bonded with the physiologically active substance into contact with a test substance.

Preferably, the substance interacting with a physiologically active substance is detected or measured by a nonelectrochemical method, and is more preferably detected or measured by surface plasmon resonance analysis.

BEST MODE FOR CARRYING OUT THE INVENTION

Figure 1:
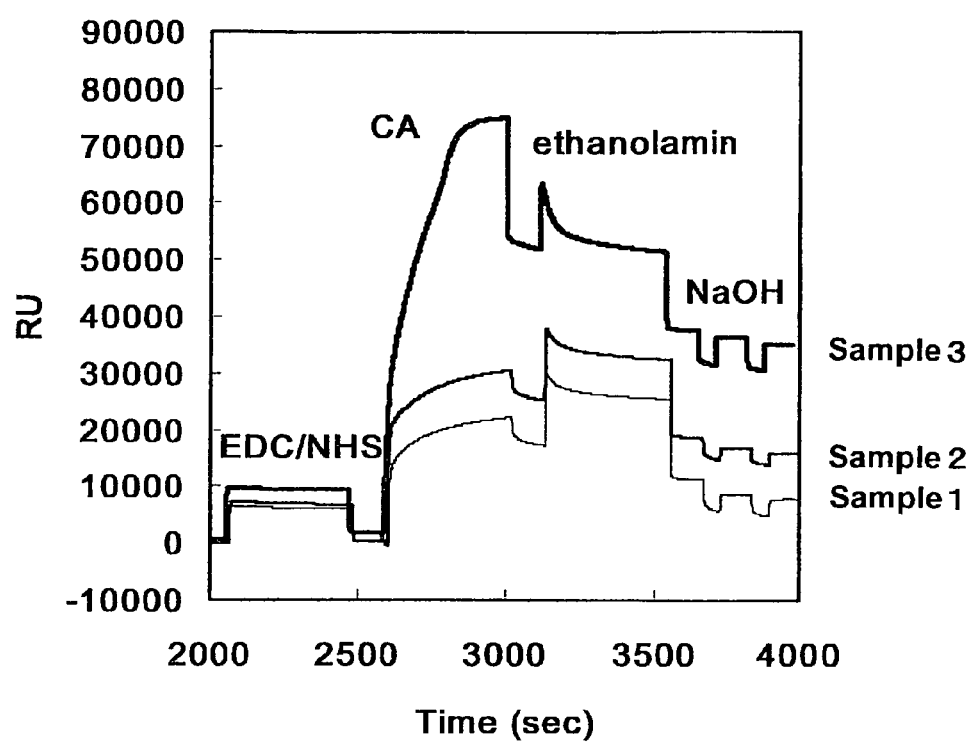
FIG. 1 is a sensorgram showing the immobilization of a protein on sensor chips obtained in Example A1.

The embodiments of the present invention will be described below.

The biosensor of the present invention has as broad a meaning as possible, and the term biosensor is used herein to mean a sensor, which converts an interaction between biomolecules into a signal such as an electric signal, so as to measure or detect a target substance. The conventional biosensor is comprised of a receptor site for recognizing a chemical substance as a detection target and a transducer site for converting a physical change or chemical change generated at the site into an electric signal. In a living body, there exist substances having an affinity with each other, such as enzyme/substrate, enzyme/coenzyme, antigen/antibody, or hormone/receptor. The biosensor operates on the principle that a substance having an affinity with another substance, as described above, is immobilized on a substrate to be used as a molecule-recognizing substance, so that the corresponding substance can be selectively measured.

In the biosensor of the present invention, a metal surface or metal film can be used as a substrate. A metal constituting the metal surface or metal film is not particularly limited, as long as surface plasmon resonance is generated when the metal is used for a surface plasmon resonance biosensor. Examples of a preferred metal may include free-electron metals such as gold, silver, copper, aluminum or platinum. Of these, gold is particularly preferable. These metals can be used singly or in combination. Moreover, considering adherability to the above substrate, an interstitial layer consisting of chrome or the like may be provided between the substrate and a metal layer.

The film thickness of a metal film is not limited. When the metal film is used for a surface plasmon resonance biosensor, the thickness is preferably between 0.1 nm and 500 nm, and particularly preferably between 1 nm and 200 nm. If the thickness exceeds 500 nm, the surface plasmon phenomenon of a medium cannot be sufficiently detected. Moreover, when an interstitial layer consisting of chrome or the like is provided, the thickness of the interstitial layer is preferably between 0.1 nm and 10 nm.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and have excellent workability are preferably used.

The substrate may be fixed and integrated on a dielectric block of a measurement unit to form a measurement chip, and this measurement chip may be formed in exchangeable manner. The example is shown below.

Figure 7:
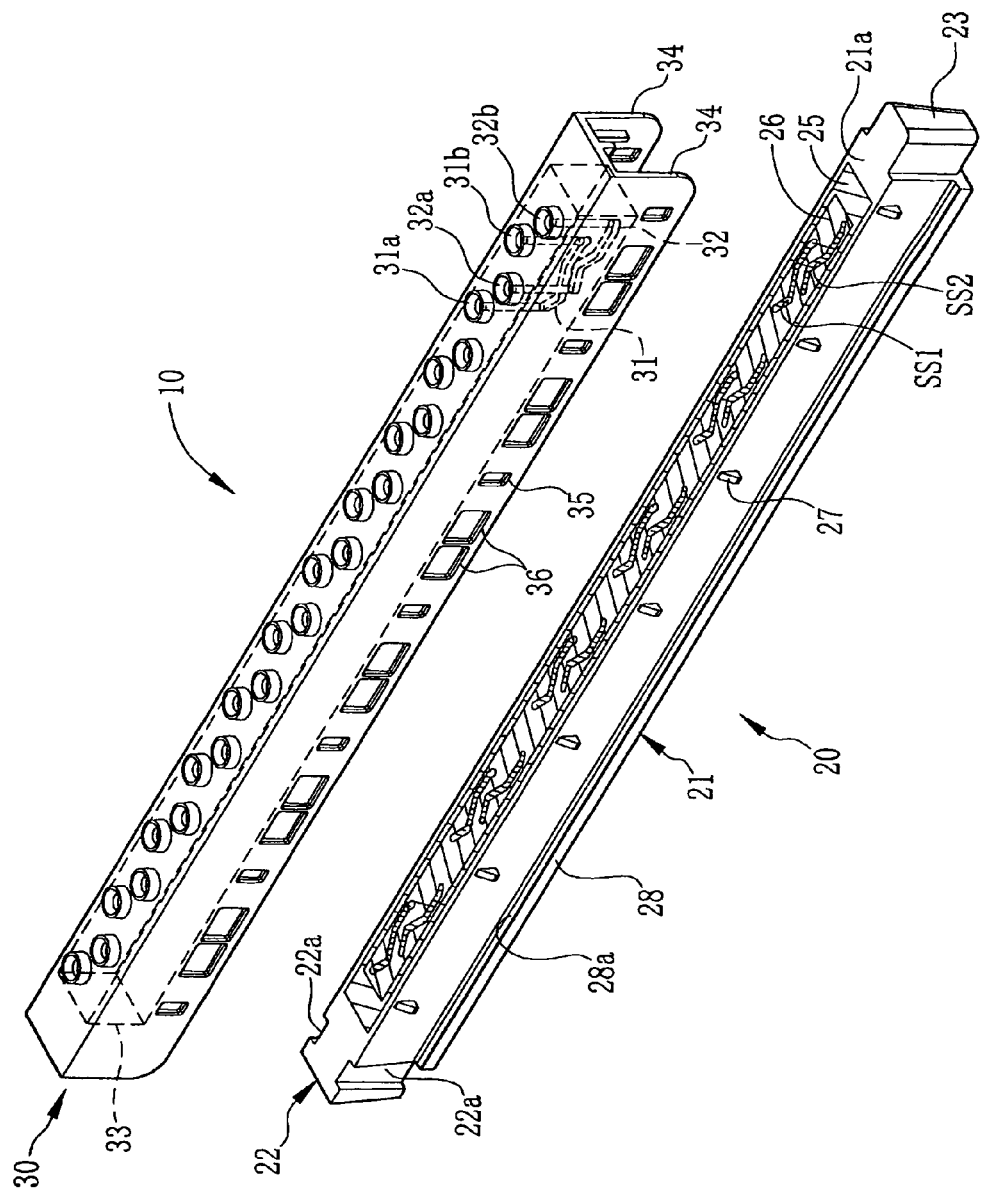
FIG. 7 is an exploded perspective view of a sensor unit. sensor unit 10, total reflection prism (optical block) 20, prism body 30, upper surface 21a, gripper part 22, groove 22a, projecting part 23, metal film (thin film layer) 25, polymer film 26, engaging nail 27, engaging part 28, engaging surface 28a, standard plane 29a, flow channel member 30, first flow channel 31, second flow channel 32, body part 33, attaching part 34, engaging pore 35, opening 36, sensor surface SS1, and sensor surface SS2 are shown.

FIG. 7 is an exploded perspective view of a sensor unit 10 which is used for measurement using SPR. The sensor unit 10 is composed of a total reflection prism (optical block) 20 which is a transparent dielectric, and a flow channel member 30 which is provided on the total reflection prism 20. The flow channel member 30 has two flow channels, namely a first flow channel 31 which is positioned at the back side in the figure, and a second flow channel 32 which is positioned at the front side in the figure. When measurement is carried out using the sensor unit 10, a measurement of one sample is carried out using 1 set of these two flow channels 31 and 32. Six of each of flow channels 31 and 32 are provided on the flow channel member 30 in a longitudinal direction, and six samples can be measured in one sensor unit 10. The number of each flow channel 31 and 32 is not limited to six, and may be 5 or less or may be 7 or more, The total reflection prism 20 is composed of a prism body 21 which is formed in long trapezoid pole, a gripper part 22 which is provided at one end of the prism body 21, and a projecting part 23 which is provided at the other end of the prism body 21. The total reflection prism 20 is die-formed by an extrusion method and the like, and the prism body 21, the gripper part 22 and the projecting part 23 are formed integrally.

The prism body 21 has a vertical section of trapezoid where upper side is longer than lower side, and collects light irradiated from the side of the bottom surface on the upper surface 21a. On the upper surface 21 of the prism body 21, a metal film (thin film layer) 25 for exciting SPR is provided. The metal film 25 has a rectangle shape in such a way that it faces each flow channel 31 and 32 of a flow channel member 30, and is formed by vapor deposition and the like. For the metal film 25, for example, gold or silver is used, and the film thickness is for example 50 nm. The film thickness of the metal film 25 is suitably selected depending on the material of the metal film 25 and the wavelength of the light which is irradiated at measurement.

On the metal film 25, a polymer film 26 is provided. The polymer film 26 has a binding group for immobilizing a physiologically active substance. A physiologically active substance is immobilized on the metal film 25 via the polymer film 26.

In the first aspect of the present invention, a metal film is coated with an organic layer having an amino group, and then a polymer containing an activated carboxyl group is allowed to be reacted with said organic layer, so that a hydrogel capable of immobilizing a physiologically active substance can be produced.

In the second aspect of the present invention, a metal film is coated with an organic layer having a functional group, and then a hydrophilic polymer having a reactive group capable of reacting with the functional group is allowed to be reacted with said organic layer, so that a hydrogel capable of immobilizing a physiologically active substance can be produced. In the present invention, examples of the functional group in the organic layer having a functional group may include amino, hydroxyl, carboxyl, aldehyde, hydrazide, carbonyl, epoxy, and vinyl groups. The amino group is preferable.

In the present invention, a method known in the art can be used as a method for coating a metal film with an organic layer having a functional group such as an amino group. A coating method using self-assembled monolayers (SAMs) is preferable in terms of convenient procedures. A coating method for a metal film using self-assembled monolayers (SAMs) has been expanded energetically by Professor Whitesides (Harvard University) et al., and its detail has been reported in, for example, Chemical Review, 105, 1103-1169 (2005). When gold is used as the metal, an alkanethiol derivative represented by the formula 1 (in the formula 1, n represents an integer of 3 to 20, and X represents a functional group) is used as an organic layer-forming compound to thereby form a monolayer having orientation in a self-assembled manner on the basis of the Au—S bond and the van der Waals force between the alkyl chains. The self-assembled monolayer is produced by a quite convenient approach wherein the gold substrate is dipped in a solution of the alkanethiol derivative. The gold surface can be coated with the organic layer having an amino group by forming a self-assembled monolayer by use of a compound represented by the formula 1 wherein $X=NH_2$.

$$HS(CH_2)_nX \qquad 1$$

Alkanethiol having an amino group at the end may be a compound comprising a thiol group and an amino group linked via an alkyl chain (formula 2) (in the formula 2, n represents an integer of 3 to 20), or may be a compound obtained by reaction between alkanethiol having a carboxyl group at the end (formula 3 or 4) (in the formula 3, n represents an integer of 3 to 20, and in the formula 4, n each independently represents an integer of 1 to 20) and a large excess of hydrazide or diamine. The reaction between alkanethiol having a carboxyl group at the end and a large excess of hydrazide or diamine may be performed in a solution state. Alternatively, the alkanethiol having a carboxyl group at the end may be bound to the substrate surface and then reacted with a large excess of hydrazide or diamine.

$$HS(CH_2)_nNH_2 \qquad 2$$

$$HS(CH_2)_nCOOH \qquad 3$$

$$HS(CH_2)_n(OCH_2CH_2)_nOCH_2COOH \qquad 4$$

The repeating number of alkyl group of the formulas 2 to 4 is preferably 3 to 20, more preferably 3 to 16, and most preferably 4 to 8. If the alkyl chain is short, formation of self-assembled monolayer becomes difficult, and if the alkyl chain is long, water solubility decreases and the handling becomes difficult.

Any compound may be used as the diamine used in the present invention. An aqueous diamine is preferable for use in the biosensor surface. Specific examples of the aqueous diamine may include aliphatic diamine such as ethylenediamine, tetraethylenediamine, octamethylenediamine, decamethylenediamine, piperazine, triethylenediamine, diethylenetriamine, triethylenetetraamine, dihexamethylenetriamine, and 1,4-diaminocyclohexane, and aromatic diamine such as paraphenylenediamine, metaphenylenediamine, paraxylylenediamine, metaxylylenediamine, 4,4'-diaminobiphenyl, 4,4'-diaminodiphenylmethane, 4,4'-diaminodiphenylketone, and 4,4'-diaminodiphenylsulfonic acid. From the viewpoint of increasing the hydrophilicity of the biosensor surface, a compound comprising two amino groups linked via an ethylene glycol unit (formula 5) may also be used. The diamine used in the present invention is preferably ethylenediamine or the compound represented by the formula 5 (in the formula 5, n and m each independently represent an integer of 1 to 20), more preferably ethylenediamine or 1,2-bis(aminoethoxy)ethane (represented by the formula 5 wherein n=2 and m=1).

$$H_2N(CH_2)_n(OCH_2CH_2)_mO(CH_2)_nNH_2 \quad 5$$

The alkanethiol having an amino group may form a self-assembled monolayer by itself or may form a self-assembled monolayer by mixing it with another alkanethiol. It is preferred for use in the biosensor surface that a compound capable of suppressing the nonspecific adsorption of a physiologically active substance should be used as the another alkanethiol. The aforementioned Professor Whitesides et al. have investigated in detail self-assembled monolayers capable of suppressing the nonspecific adsorption of a physiologically active substance and have reported that a self-assembled monolayer formed from alkanethiol having a hydrophilic group is effective for suppressing nonspecific adsorption (Langmuir, 17, 2841-2850, 5605-5620, and 6336-6343 (2001)). In the present invention, any of compounds described in the aforementioned papers may be used preferably as the alkanethiol that forms a mixed monolayer with the alkanethiol having an amino group. In terms of excellent ability to suppress nonspecific adsorption and ease of acquisition, it is preferred that alkanethiol having a hydroxyl group (formula 6) or alkanethiol having an ethylene glycol unit (formula 7) (in the formula 6, n represents an integer of 3 to 20, and in the formula 7, n and m each independently represent an integer of 1 to 20) should be used as the alkanethiol that forms a mixed monolayer with the alkanethiol having an amino group.

$$HS(CH_2)_nOH \quad 6$$

$$HS(CH_2)_n(OCH_2CH_2)_mOH \quad 7$$

When alkane thiol having an amino group is mixed with another alkane thiol to form a self-assembled monolayer, the repeating number of alkyl group of the formulas 2 to 4 is preferably 4 to 20, more preferably 4 to 16, and most preferably 4 to 10. Further, the repeating number of alkyl group of the formulas 6 and 7 is preferably 3 to 16, more preferably 3 to 12, and most preferably 3 to 8.

In the present invention, the alkanethiol having an amino group and the alkanethiol having a hydrophilic group may be mixed at any ratio. If the proportion of the alkanethiol having an amino group is small, the binding amount of the polymer containing an activated carboxyl group is decreased. If the proportion of the alkanethiol having a hydrophilic group is small, the ability to suppress nonspecific adsorption is reduced. Hence, the alkanethiol having an amino group and the alkanethiol having a hydrophilic group are mixed preferably at a ratio ranging from 1/1 to 1/1,000,000, more preferably at a ratio ranging from 1/4 to 1/10,000, even more preferably at a ratio ranging from 1/10 to 1/1,000. From the viewpoint of reducing steric hindrance in reaction with the polymer containing an active esterified carboxyl group, it is preferred that the alkanethiol having an amino group should have a molecular length larger than that of the alkanethiol having a hydrophilic group.

Any of compounds synthesized on the basis of the review by Professor Grzybowski (Northwestern University) et al. (Curr. Org. Chem., 8, 1763-1797 (2004)) and documents cited therein, or a commercially available compound may be used as the alkanethiol used in the present invention. These compounds can be purchased from Dojindo Laboratories, Aldrich, SensoPath Technologies, Frontier Scientific Inc., and so on. In the present invention, a disulfide compound, an oxidation product of alkanethiol, may be used as with the alkanethiol.

Any synthetic polymer containing a carboxyl group and any polysaccharide containing a carboxyl group may be used as the polymer containing a carboxyl group used in the present invention. Examples of the synthetic polymer containing a carboxyl group include polyacrylic acid, polymethacrylic acid, and copolymers thereof, for example, a methacrylic acid copolymer, acrylic acid copolymer, itaconic acid copolymer, crotonic acid copolymer, maleic acid copolymer, partially esterified maleic acid copolymer, and an acid anhydride addition product of a polymer having a hydroxyl group, as described in the specifications of JP Patent Publication (Kokoku) No. 59-44615B (1984), JP Patent Publication (Kokoku) Nos. 54-34327B (1979), 58-12577B (1983), and 54-25957B (1979), and JP Patent Publication (Kokai) Nos. 59-53836A (1984) and 59-71048A (1984). The polysaccharides containing a carboxyl group may be any of extracts from natural plants, products of microbial fermentation, products synthesized by enzymes, and chemically synthesized products. Specific examples thereof may include hyaluronic acid, chondroitin sulfate, heparin, dermatan acid sulfate, carboxymethyl cellulose, carboxyethyl cellulose, cellouronic acid, carboxymethyl chitin, carboxymethyl dextran, and carboxymethyl starch. A commercially available compound may be used as the polysaccharides containing a carboxyl group. Concrete examples thereof may include carboxymethyl dextran CMD, CMD-L, and CMD-D40 (manufactured by Meito Sangyo), carboxymethyl cellulose sodium (manufactured by Wako Pure Chemical Industries, Ltd.), and sodium alginate (manufactured by Wako Pure Chemical Industries, Ltd.).

The polymer containing a carboxyl group is preferably the polysaccharide containing a carboxyl group, more preferably carboxymethyl dextran.

The molecular weight of the polymer containing a carboxyl group used in the present invention is not particularly limited. The polymer containing a carboxyl group has preferably an average molecular weight of 1,000 to 5,000,000, more preferably an average molecular weight of 10,000 to 2,000,000, even more preferably an average molecular weight of 100,000 to 1,000,000. If the average molecular weight is small than this range, the amount of immobilization of a biologically active substance is lowered. If the average molecular weight is larger than this range, the polymer is difficult to handle due to high solution viscosity.

An approach known in the art, for example, a method wherein a carboxyl group is activated with 1-(3-dimethylaminopropyl)-3-ethylcarbodiimide (EDC) (aqueous carbodiimide) and N-hydroxysuccinimide (NHS), a method wherein a carboxyl group is activated with EDC alone, a method described in Japanese Patent Application No. 2004-238396 (JP Patent Publication (Kokai) No. 2006-58071) (i.e., a method wherein a carboxyl group is activated with any compound selected from a uronium salt, phosphonium salt, and triazine derivative having a particular structure), and a method described in Japanese Patent Application No. 2004-275012 (JP Patent Publication (Kokai) No. 2006-90781) (i.e., a method wherein a carboxyl group is activated with a carbodiimide derivative or salt thereof and then activated with any compound selected from a nitrogen-containing heteroaromatic compound having a hydroxyl group, phenol derivative having an electron-withdrawing group, and aromatic compound having a thiol group) can be used preferably as a method for activating the polymer comprising a carboxyl group. The polymer containing a carboxyl group activated by any of these approaches can be reacted with the substrate having an amino group to thereby produce the biosensor of the present invention.

The uronium salt, phosphonium salt, and triazine derivative having a particular structure in Japanese Patent Application No. 2004-238396 (JP Patent Publication (Kokai) No. 2006-58071) refer to a uronium salt represented by the formula 1 below, phosphonium salt represented by the formula 2 below, and triazine derivative represented by the formula 3 below, respectively.

Formula 1

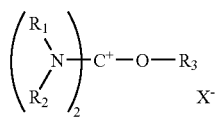

Formula 2

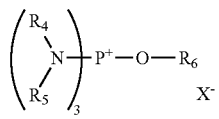

Formula 3

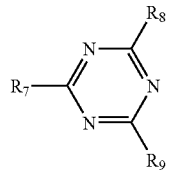

In the formula 1, $R_1$ and $R_2$ each independently represent an alkyl group containing 1 to 6 carbon atoms or together form an alkylene group containing 2 to 6 carbon atoms and form a ring with a N atom, $R_3$ represents an aromatic ring group containing 6 to 20 carbon atoms or a heterocyclic group containing at least one or more heteroatom, and $X^-$ represents an anion. In the formula 2, $R_4$ and $R_5$ each independently represent an alkyl group containing 1 to 6 carbon atoms or together form an alkylene group containing 2 to 6 carbon atoms and form a ring with a N atom, $R_6$ represents an aromatic ring group containing 6 to 20 carbon atoms or a heterocyclic group containing at least one or more heteroatom, and $X^-$ represents an anion. In the formula 3, $R_7$ represents an onium group, and $R_8$ and $R_9$ each independently represent an electron donating group.

Further, as a method for activating a polymer containing a carboxyl group, a method using a nitrogen-containing compound may be used. Specifically, nitrogen-containing compound of the following formula (Ia) or (Ib) may be used:

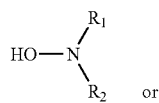

(Ia)

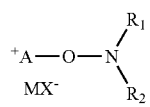

(Ib)

wherein $R_1$ and $R_2$ each independently represents a carbonyl group, a carbon atom or a nitrogen atom, which may have a substituent, or $R_1$ and $R_2$ may be bound to form a 5- or 6-membered ring, A represents a carbon atom or a phosphorus atom, which has a substituent, M represents an (n−1) valent element, and X represents a halogen atom.

Here, $R_1$ and $R_2$ each independently represents a carbonyl group, a carbon atom or a nitrogen atom, which may have a substituent, and preferably $R_1$ and $R_2$ may be bound to form a 5- or 6-membered ring. Particularly preferred are hydroxysuccinic acid, hydroxyphthalic acid, 1-hydroxybenzotriazol, 3,4-dihydroxy-3-hydroxy-4-oxo-1,2,3-benzotriazine, and derivatives thereof.

Further, the following nitrogen-containing compounds can be preferably used.

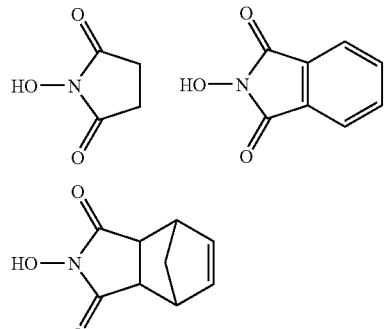

Preferably, as the nitrogen-containing compound, the compound of the following formula (II) wherein Y and Z each independently represents CH or a nitrogen atom, can be used.

Formula (II)

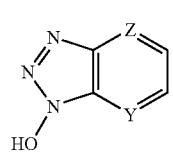

Preferably, the following compounds can be used.

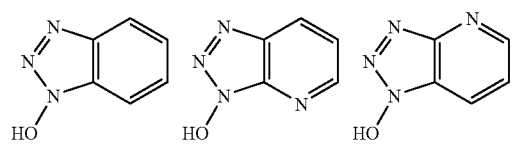

Preferably, as the nitrogen-containing compound, the following compound can be used.

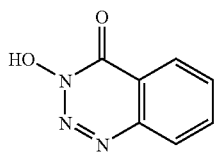

Preferably, the compound of the following formula (III) wherein A represents a carbon atom or a phosphorus atom, which has a substituent, Y and Z each independently represents CH or a nitrogen atom M represents an (n−1) valent element, and X represents a halogen atom, can be used.

Formula (III)

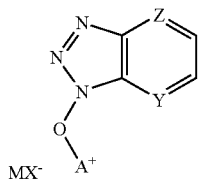

The substituent on the carbon atom or the phosphorus atom which is represented by A is preferably an amino group which has a substituent, and dialkylamino group such as dimethylamino group or pyrrolidino group is preferred. The (n−1) valent element represented by M may include phosphorus atom, boron atom, and arsenic atom, and preferably phosphorus atom. The halogen atom represented by X may include fluorine atom, chlorine atom, bromine atom and iodine atom, and preferably fluorine atom.

As the specific examples of the nitrogen-containing compound of the formula (III) may include the following compounds.

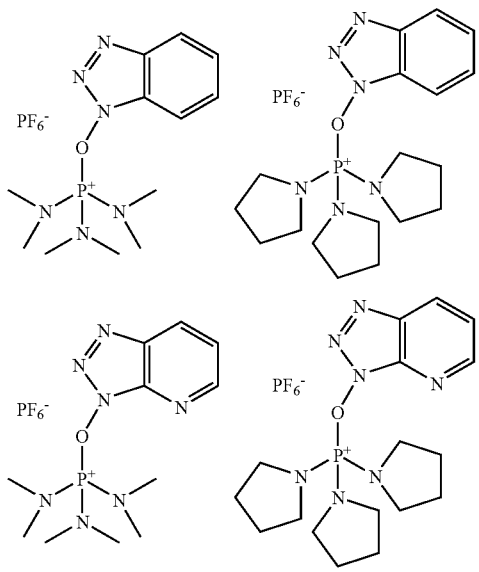

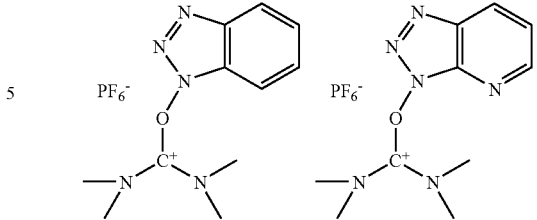

Preferably, as the nitrogen-containing compound, the compound of the following formula (IV) wherein A represents a carbon atom or a phosphorus atom, which has a substituent, M represents an (n−1) valent element, and X represents a halogen atom, can be used Formula (IV)

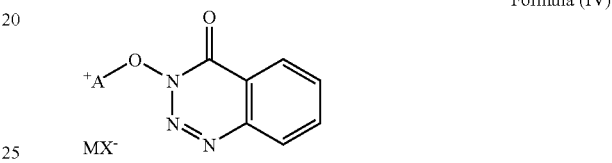

Specifically, the following compound and the like can be used.

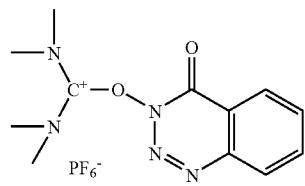

Further, as a method for activating a polymer containing a carboxyl group, a phenol derivative having an electron-withdrawing group is preferably used. The σ value of the electron-withdrawing group is preferably 0.3 or more. Specifically, the following compounds can be used.

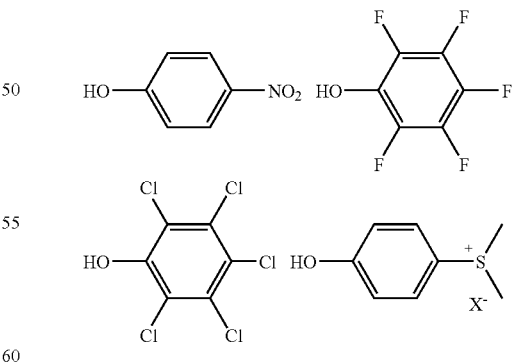

Further, as a method for activating a polymer containing a carboxyl group, a carbodiimide derivative may be used in combination. Preferably, a water soluble carbodiimide derivative may be used in combination. More preferably, the following compound (1-Ethyl-3-(3-dimethylaminopropyl) carbodiimide, hydrochloride) may be used in combination.

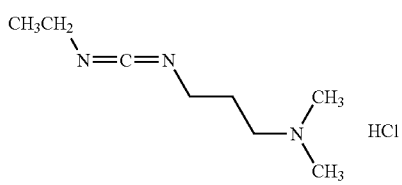

The aforementioned carbodiimide derivative, nitrogen-containing compound or phenol derivative may be used in combination, or each may be used alone if desired. Preferably, a combination of the carbodiimide derivative and the nitrogen-containing compound is used.

Further, as a method for activating a polymer containing a carboxyl group, the following compound may be used. This compound may be used alone, or may be used in combination with a carbodiimide derivative, a nitrogen-containing compound or a phenol derivative.

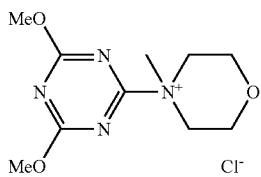 [SMILES: COc1nc(OC)nc([N+]2(C)CCOCC2)n1 ; [Cl-]]

A polymeric hardener for silver halide photography, a hydrophilic polymer having an acetoacetyl group, and a polymer containing activated carboxylic acid can be preferably used as the hydrophilic polymer having a reactive group capable of reacting with the functional group on substrate surface which is used in the second aspect of the present invention. As the polymer containing activated carboxylic acid, those mentioned hereinabove can be used. The polymeric hardener and the hydrophilic polymer having an acetoacetyl group which can be used in the present invention are described below.

A polymeric hardener is a polymer compound that has, within a molecule, a plurality of reactive functional groups that undergo binding reaction with a hydrophilic colloid such as gelatin. Such polymeric hardener is described in the following documents: JP Patent Publication (Kokai) No. 56-66841 A (1981), GB Patent No. 1,322,971, U.S. Pat. No. 3,671,256, JP Patent Publication (Kokai) No. 7-64226 A (1995), JP Patent Publication (Kokai) No. 7-140596 A (1995), JP Patent Publication (Kokai) No. 10-111545 A (1998), JP Patent Publication (Kokai) 2000-62629 A, JP Patent Publication (Kokai) No. 2004-20919 A, The Theory of the Photographic Process (written by James, 4$^{th}$ edition, page 84, 1977, Macmillan Publishers Limited), Polymeric Amine and Ammonium Salts (written by Campbelletal et al., pages 321 to 332, 1979, Pergamon Press, Ltd.), and the like.

A polymeric hardener that is used in the present invention is a polymer compound having a reactive functional group capable of binding to a functional group on the surface of a biosensor. Such polymeric hardener is preferably a polymer compound having a reactive functional group represented by the following formulae (1) to (9).

—SO$_2$CH=CH$_2$  Formula (1)

—SO$_2$CH$_2$CH$_2$X  Formula (2)

In formula (2), X is a group (e.g., —Cl, —OSO$_2$CH$_3$, —OSO$_2$C$_6$H$_4$CH$_3$, —OCOCH$_3$, —OSO$_3^-$, or pyridinium) that is eliminated by substitution reaction or elimination reaction when the functional group represented by formula (2) reacts with a nucleophilic reagent or a base.

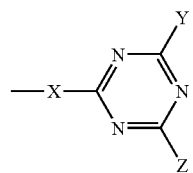

Formula (3)

In formula (3), X represents a single bond, —O—, or —NR— and R represents a hydrogen atom, an alkyl group, or an aralkyl group. Y and Z each represent a halogen atom (e.g., a chlorine atom or a bromine atom), an alkoxy group (e.g., methoxy), a hydroxyl group or a salt thereof, or an amino group that may be substituted. At least one of Y and Z is a halogen atom.

—CHO  Formula (4)

Formula (5):

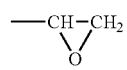

—NCO  Formula (6)

—NHCONHCOCH=CH$_2$  Formula (7)

—NHCONHCOCH$_2$CH$_2$X  Formula (8)

In the formula, X is as defined in formula (2).

—COX  Formula (9)

In the formula, X is a group (e.g., one of the following groups) that is easily eliminated when the functional group represented by formula (9) reacts with an amino group.

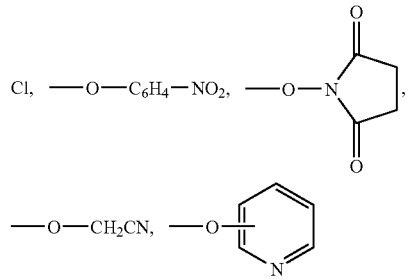

Formula (9) represents a group that is generally known as an active ester group or a mixed anhydride.

A polymerization method used upon production of a polymeric hardener that is used in the present invention is not particularly restricted. For example, such hardener can be produced by a condensation polymerization method. Furthermore, such hardener may also be produced by a method such as radical polymerization or anionic polymerization using compounds having ethylene unsaturated bonds. Furthermore, such hardener may also be produced by introducing the above reactive functional groups into natural polymers (e.g., starch, dextran, and gelatin). A method for introducing a functional group (functional groups represented by the above formulae (1) to (9) and hereinafter referred to as reactive functional groups) that are capable of reacting with a hydrophilic colloid that is used in the present invention is also not particularly restricted. A polymer may also be produced by performing polymerization reaction using monomers having a reactive functional group. Furthermore, a polymer may be previously produced and then the above reactive functional group may also be introduced by so-called polymer reaction. Furthermore, a method that involves performing polymerization reaction using a monomer compound having precursors of a reactive functional group and then generating a reactive functional group by an appropriate method is also effective.

A polymeric hardener that is used in the present invention may also be produced by radically polymerizing monomers having the above reactive functional group (or precursor thereof) and the ethylene unsaturated bond within the same molecule. Typical examples of monomers having a reactive functional group are compounds listed below.

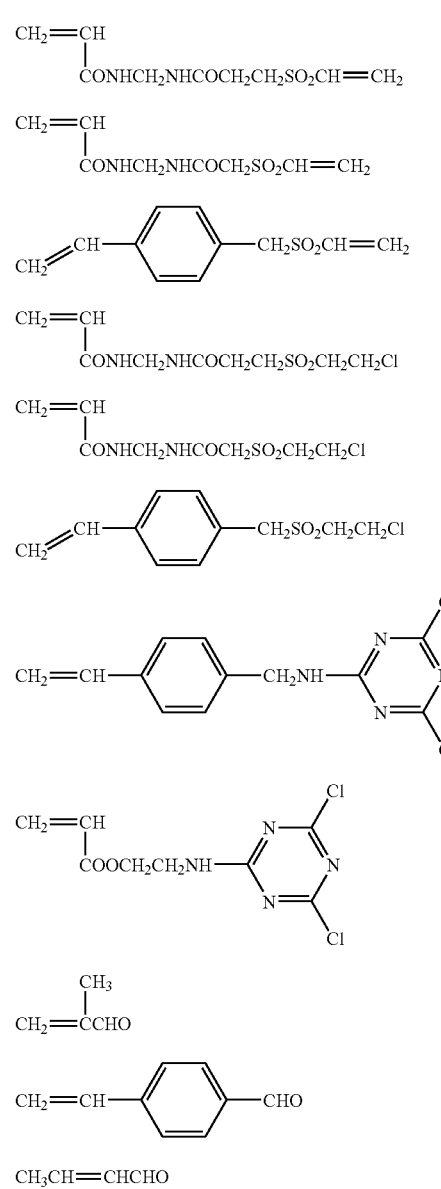
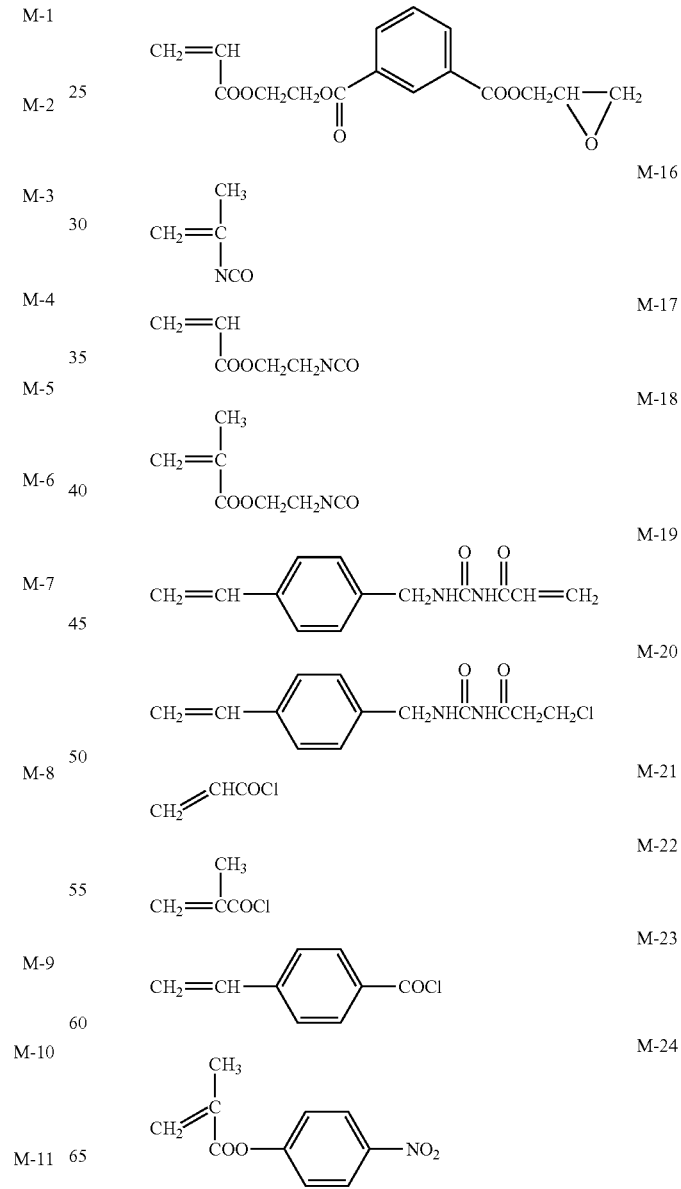

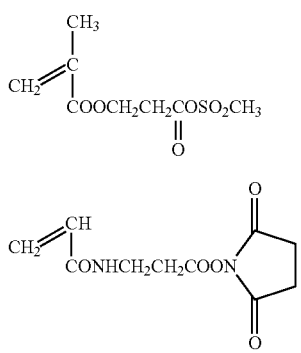

A polymer that is used in the present invention may be a homopolymer of a monomer having a reactive functional group, or a copolymer of such monomer and another one or two or more different types of monomer. In the case of such copolymer, the proportion of a monomer having a reactive functional group in such copolymer is 1 weight % or more and preferably 5 weight % or more. Radical copolymerization is not particularly limited, as long as the other monomer(s) are radically polymerizable. Specific examples of such monomer include monomers listed below. Furthermore, when the other monomer(s) have a functional group capable of undergoing reaction, it is preferable to select an appropriate combination of monomers within a range such that no reactions are caused to take place upon copolymerization with the functional groups represented by the above formulae (1) to (9).

Such specific examples are: acrylic acid, methacrylic acid, and the esters thereof (e.g., acrylic acid, methylacrylate, butylacrylate, benzylacrylate, hydroxyethylacrylate, $CH_2=CHCOO(CH_2CH_2O)_nR$ (where R is a hydrogen atom or an alkyl group and n is an integer of 1 or greater), methacrylic acid, methyl methacrylate, ethyl methacrylate, benzyl methacrylate, hydroxyethyl methacrylate, 2-ethylhexyl methacrylate, 2-methoxyethyl methacrylate, N,N-dimethylaminoethyl methacrylate, and 2-sulfoethyl methacrylate); amides of ethylene unsaturated carboxylic acid (e.g., acrylamide, methacrylamide, N-acryloyl morpholine, N,N-dimethylacrylamide, and 2-acrylamide-2-methylpropane sulfonate (or a salt thereof));
aromatic monomers (e.g., styrene, vinyltoluene, p-t-butylstyrene, p-vinylbenzoic acid, and vinylnaphthalene); and
other vinyl monomers (e.g., ethylene, propylene, vinyl chloride, vinylidene chloride, triphloroethylene, triphlorochloroethylene, vinyl acetate, vinyl propionate, vinyl alcohol, N-vinyl pyrrolidone, N-vinylacetoamide, acrylonitrile, and methacrylonitrile).

Specific examples of a polymeric hardener that is used in the present invention will be listed below, but the present invention is not limited by these examples. The copolymerization ratio of each compound represents a weight percentage.

P-1: M-1/2-acrylamide-2-methylpropane sodium sulfonate copolymer (10/90)
P-2: M-1/2-acrylamide-2-methylpropane sodium sulfonate copolymer (30/70)
P-3: M-1/2-acrylamide-2-methylpropane sodium sulfonate copolymer (50/50)
P-4: M-1/methylmethacrylate copolymer (20/80)
P-5: M-2/sodium acrylate copolymer (30/70)
P-6: M-2/2-hydroxyethyl methacrylate copolymer (20/80)
P-7: M-3/butylacrylate copolymer (60/40)
P-8: M-4/2-acrylamide-2-methylpropane sodium sulfonate copolymer (30/70)
P-9: M-6/ethylacrylate copolymer (60/40)
P-10: M-7/N-vinyl pyrrolidone copolymer (20/80)
P-11: M-7/diacetoneacrylamide copolymer (10/90)
P-12: M-10/sodium methacrylate copolymer (15/85)
P-13: M-10/methylacrylate/methylmethacrylate copolymer (20/40/40)
P-14: M-12/ethyl methacrylate copolymer (33/67)
P-15: M-12/2-acrylamide-2-methylpropane sodium sulfonate copolymer (15/85)
P-16: M-13/methyl methacrylate copolymer (33/67)
P-17: M-13/2-acrylamide-2-methylpropane sodium sulfonate copolymer (20/80)
P-18: M-13/N-acryloyl morpholine copolymer (20/80)
P-19: M-13/methoxypolyethylene glycol (23 mer) monomethacrylate copolymer (50/50)
P-20: M-18/N,N-dimethylacrylamide copolymer (5/95)
P-21: M-18/butylmethacrylate copolymer (30/70)
P-22: M-18/styrene/butylacrylate copolymer (20/30/50)
P-23: M-19/2-acrylamide-2-methylpropane sodium sulfonate copolymer (20/80)
P-24: M-23/methylacrylate copolymer (20/80)
P-25: M-24/ethylacrylate/styrene copolymer (20/50/30)
P-26: M-26/acrylamide copolymer (25/75)
P-27: M-26/N,N-dimethylaminoethyl methacrylate copolymer (30/70)

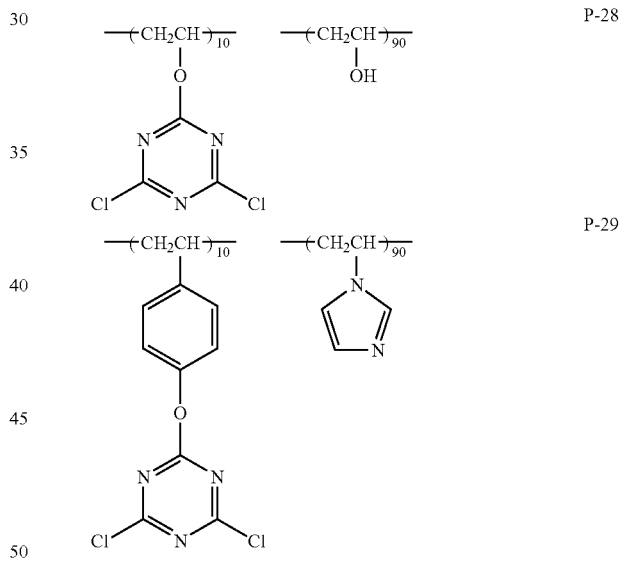

As a polymeric hardener having a reactive functional group, which is used in the present invention, preferably, an active olefin type polymeric hardener, an s-triazine type polymeric hardener, an active halogen type polymeric hardener, an aldehyde type polymeric hardener, a glycidyl type polymeric hardener, or the like is used. Further preferably, an active olefin type polymeric hardener or a precursor thereof, an s-triazine type polymeric hardener, or a glycidyl type polymeric hardener is used. A vinylsulfone type polymeric hardener, a precursor thereof, or a dichlorotriazine type polymeric hardener is particularly preferable.

A polymeric hardener in the present invention is immobilized on the surface of a biosensor, in order to form hydrogel. Accordingly, it is desirable that such polymer have hydrophilic groups other than the reactive functional groups. Specific examples of such hydrophilic groups include nonionic groups such as a hydroxyl group and an ethylene glycol group, anionic groups such as a sulfonic acid group, a carboxylic acid group, and a phosphoric acid group, cationic groups such as a quaternary ammonium group and a pyridinium group, and dipolar ionic groups such as a phosphorylcholine group.

Examples of monomer units having a hydrophilic group in the present invention include the following monomers:

monomers having an nonionic group (e.g., 2-hydroxyethylacrylate, 2-hydroxyethyl methacrylate, hydroxypropyl acrylate, hydroxypropylmethacrylate, 2-hydroxy-3-chloropropylacrylate, β-hydroxyethyl β'-acryloyloxyethylphthalate, 1,4-butylene glycol monoacrylate, hydroxystyrene, allylalcohol, methallyl alcohol, isopropenyl alcohol, and 1-butenyl alcohol);

monomers having an anionic group (e.g., vinyl sulfonic acid, methallylsulfonic acid, 2-acrylamide-2-methylpropane sulfonic acid, sulfoethyl methacrylate, styrenesulfonic acid, acrylic acid, methacrylic acid, and 2-(phosphonoethyloxy) ethyl methacrylate);

monomers having a cationic group (e.g., [2-(acryloyloxy) ethyl]trimethyl ammonium chloride and [2-(methacryloyloxy)ethyl]trimethyl)ammonium chloride; and monomers having a dipolar ionic group (e.g., [2-(methacryloyloxy)ethyl]dimethyl-(3-sulfopropyl)ammonium hydroxide and [2-(methacryloyloxy)ethyl]phosphorylcholine).

Introduction of cationic group or anionic group into a polymeric hardener enables concentration of a physiologically active substance having opposite charge on a detection surface using electrostatic interaction. For example, in the case of a protein that has been dissolved in a buffer with a pH higher than the isoelectric point, the protein is electrostatically concentrated on the hydrogel surface to which a polymeric hardener having a cationic group has been bound. Thus, it becomes possible to efficiently bind the protein to the reactive functional group. In contrast, in the case of protein that has been dissolved in a buffer with a pH lower than the isoelectric point, the protein is electrostatically concentrated on the hydrogel surface to which a polymeric hardener having an anionic group has been bound. Thus, it also becomes possible to efficiently bind the protein to reactive functional groups. Specific examples of compounds having such a structure may include compounds described below. Moreover, compounds described in JP Patent Publication (Kokai) Nos. 54-65033A (1979), 56-142524A (1981), and 60-61742A (1985) can also be used preferably.

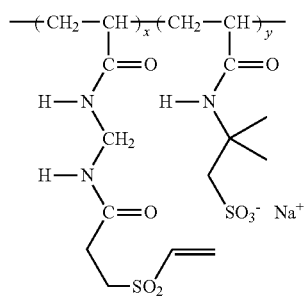

P-30

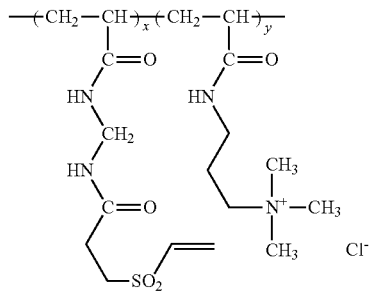

P-31

Hereafter, an acetoacetyl group-containing hydrophilic polymer that can be used in the present invention will be explained. An acetoacetyl group-containing water-soluble polymer has the property of reacting with a crosslinking agent having a plurality of aldehyde groups, amino groups, hydrazide groups or the like, at room temperature, so that it becomes hardened. Therefore, it becomes possible to instantly adhere two substrates to each other by applying an acetoacetyl group-containing water-soluble polymer on the surface of one substrate and applying a crosslinking agent on the surface of another substrate, and then by pressing both surfaces. Also, by adding a crosslinking agent to an aqueous solution that contains an acetoacetyl group-containing water-soluble polymer and mixing them, an irrefrangible gel with extremely large water content can be easily obtained at room temperature. JP Patent Publication (Kokai) No. 5-112771 A (1993), JP Patent Publication (Kokai) No. 5-156220 A (1993), JP Patent Publication (Kokai) No. 2002-285117 A, and the like disclose that an acetoacetyl group-containing water-soluble polymer has an excellent property as a water-soluble adhesive.

A method for producing an acetoacetyl group-containing water-soluble polymer will be explained below. Known methods for producing acetoacetylated polyvinyl alcohol, which is a typical compound as an acetoacetyl group-containing water-soluble polymer, include: a method of adding diketene gas to acetic acid in a state where a polyvinyl alcohol resin is dispersed in the acetic acid; a method of adding diketene gas to a solution in which polyvinyl alcohol resin is dissolved in a solvent such as dimethylformamide or dioxane; a method of allowing polyvinyl alcohol powders to directly react with diketene gas; and a method of allowing polyvinyl alcohol to react with an acetoacetic acid ester in a solution for interesterification. The acetoacetylated polyvinyl alcohol used in the present invention can be synthesized by the method described in JP Patent Publication (Kokai) No. 2002-285117 A, for example. Alternatively, commercially available acetoacetylated polyvinyl alcohols such as Gohsefimer Z100, Z200, Z200H, Z210, Z320, or the like, which are made by The Nippon Synthetic Chemical Industry Co., Ltd., can also be used.

Also, an acetoacetyl group-containing water-soluble polymer can be produced via copolymerization of an acetoacetyl group-containing monomer with a water-soluble monomer. Examples of such an acetoacetyl group-containing monomer may include acetoacetoxyethyl acrylate, acetoacetoxyethyl methacrylate, acetoacetoxyethyl crotonate, acetoacetoxypropyl acrylate, acetoacetoxypropyl methacrylate, acetoacetoxypropyl crotonate, 2-cyanoacetoacetoxyethyl methacrylate, N-(2-acetoxyethyl) acrylamide, N-(2-acetoxyaminoethyl) methacrylamide, allyl acetoacetate, and vinyl acetoacetate. These monomers can be produced via a reaction between a functional group-containing ethylene unsaturated monomer and diketene, via a transesterification of the above monomer with an acetoacetoxyalkyl ester, or the like. The acetoacetyl group-containing water-soluble polymer in the invention can be synthesized by the method described in Japanese Patent No. 2777732, for example.

In the present invention, as an acetoacetyl group-containing water-soluble polymer, it is possible to use copolymers with various monomers, other than the aforementioned acetoacetyl group-containing monomer. The monomer unit for such copolymer includes the following monomers:

acrylic acid, methacrylic acid, and their esters: such as acrylic acid, methyl acrylate, butyl acrylate, benzyl acrylate, hydroxyethyl acrylate, $CH_2=CHCOO(CH_2CH_2O)_nR$ (wherein R is a hydrogen atom and an alkyl group, and n is an integer of 1 or greater), methacrylic acid, methyl methacrylate, ethyl methacrylate, benzylmethacrylate, hydroxyethyl methacrylate, 2-ethylhexyl methacrylate, 2-methoxyethyl methacrylate, N,N-dimethylaminoethyl methacrylate, and 2-sulfoethyl methacrylate;

amides of ethylene unsaturated carboxylic acid: such as acrylamide, methacrylamide, N-acryloyl morpholine, N,N-dimethylacryl amide, and 2-acrylamide-2-methylpropanesulfonic acid (or its salt);

aromatic monomers: such as styrene, vinyl toluene, p-t-butylstyrene, p-vinyl benzoic acid, or vinylnaphthalene; and other vinyl monomers: such as ethylene, propylene, vinyl chloride, vinylidene chloride, trifluoroethylene, trifluorochloroethylene, vinyl acetate, vinyl propionate, vinyl alcohol, N-vinyl pyrrolidone, N-vinylacetamide, acrylonitrile, or methacrylonitrile.

In the invention, an acetoacetyl group-containing hydrophilic polymer is immobilized on the surface of a biosensor, so as to form a hydrogel thereon. Therefore, it is preferable that such an acetoacetyl group-containing hydrophilic polymer have a hydrophilic group as well as a reactive functional group. Specific examples of such a hydrophilic group may include nonionic groups such as a hydroxyl group or an ethylene glycol group, anionic groups such as a sulfonic group, a carboxylic acid, or a phosphate group, cationic groups such as a quaternary ammonium group or a pyridinium group, and zwitterionic groups such as phosphoryl choline group.

In the invention, monomer units having a hydrophilic group include the following monomers:

monomers having a nonionic group: 2-hydroxyethyl acrylate, 2-hydroxyethyl methacrylate, hydroxypropyl acrylate, hydroxypropyl methacrylate, 2-hydroxy-3-chloropropyl acrylate, β-hydroxyethyl-β'-acryloyloxyethyl phthalate, 1,4-butylene glycol monoacrylate, hydroxystyrene, allyl alcohol, methallyl alcohol, isopropenyl alcohol, 1-butenyl alcohol, or the like;

monomers having an anionic group: vinylsulfonic acid, methallylsulfonic acid, 2-acrylamide-2-methylpropanesulfonic acid, sulfoethyl methacrylate, styrenesulfonic acid, acrylic acid, methacrylic acid, 2-(phosphonoethyloxy)ethyl methacrylate, or the like;

monomers having a cationic group: [2-(acryloyloxy)ethyl]trimethylammonium chloride, [2-(methacryloyloxy)ethyl]trimethylammonium chloride, or the like; and monomers having a zwitterionic group: [2-(methacryloyloxy)ethyl]dimethyl-(3-sulfopropyl)ammonium hydroxide, 2-[(methacryloyloxy)ethyl]phosphorylcholine, or the like.

By introducing a cationic group or an anionic group into an acetoacetyl group-containing water-soluble polymer, a physiologically active substance having opposite charges can be concentrated onto a detection surface via an electrostatic interaction. In the case of a protein dissolved in a buffer solution having a pH that is higher than an isoelectric point, for example, since such a physiologically active substance is electrostatically concentrated onto a hydrogel surface, to which an acetoacetyl group-containing hydrophilic polymer having a cationic group is bound, it can be effectively bonded to a reactive functional group. On the other hand, in the case of a protein dissolved in a buffer solution having a pH that is lower than an isoelectric point, since such a physiologically active substance is electrostatically concentrated onto a hydrogel surface, to which an acetoacetyl group-containing water-soluble polymer having an anionic group is bound, it becomes possible to allow the physiologically active substance to efficiently react with an acetoacetyl group or a carboxylic acid introduced by allowing such an acetoacetyl group to react with amino acid.

In the first aspect of the present invention, the polymer containing an activated carboxyl group may be reacted as a solution with the substrate or may be reacted with the substrate in a state of thin film of the polymer formed on the substrate by use of an approach such as spin coating. Preferably, the polymer containing an activated carboxyl group is a polymer containing an active esterified carboxyl group. The reaction in a state of the thin film is preferable. Further, the second aspect of the present invention is characterized in that the hydrophilic polymer having a reactive group in a thin film state is brought into contact with the substrate. A method known in the art may be used as a method for forming the thin film on the substrate, and specifically, an extrusion coating method, curtain coating method, casting method, screen printing method, spin coating method, spray coating method, slide bead coating method, slit and spin system, slit coating system, die coating method, dip coating method, knife coating method, blade coating method, flow coating method, roll coating method, wire bar coating system, transfer printing method, and the like may be used. These methods for forming the thin film have been described in, for example, "Progress of Coating Technique", Yuji Harazaki, United Engineering Center (1988), "Coating Technology", Technical Information Institute (1999), "Aqueous Coating Technique" CMC Publishing (2001), "Evolving Organic Thin Film, —Film Formation—" Sumibe Techno Research (2004), and "Polymer Surface Processing", Satoru Iwamori, Gihodo Shuppan (2005). In the present invention, the method for forming the thin film on the substrate is preferably the spray coating method or spin coating method, more preferably the spin coating method, since a thickness-controlled coating film can be easily produced by such method.

The spray coating method is a method wherein a substrate is moved with an ultra-atomized polymer solution sprayed onto the substrate to thereby uniformly coat the polymer solution onto the substrate. When the trigger of a spray gun is pulled, an air valve and a needle valve are simultaneously opened. The polymer solution is ejected in the form of a fine mist from a nozzle, and this polymer solution in the form of a fine mist is further ultra-atomized by air ejected from an air cap located at the end of the nozzle. A thickness-controlled polymer film is easily produced by forming the coating film of the ultra-atomized polymer solution on the substrate surface, followed by the evaporation of the solvent. The thickness of the polymer thin film can be controlled on the basis of the concentration of the polymer solution, the moving speed of the substrate, and so on.

The spin coating method is a method wherein a polymer solution is added dropwise onto a substrate placed horizontally, which is then spun at a high speed to thereby uniformly coat the polymer solution onto the whole surface of the substrate through a centrifugal force. A thickness-controlled polymer film is easily produced with the scattering of the polymer solution through a centrifugal force and the evaporation of the solvent. The thickness of the polymer thin film can be controlled on the basis of the revolution speed, the concentration of the polymer solution, the vapor pressure of the solvent, and so on. In the present invention, the revolution speed during spin coating is not particularly limited. If the revolution speed is too small, the solution remains on the substrate. If the revolution speed is too large, an available apparatus is restricted. Hence, in the present study, the revolution speed during spin coating is preferably 500 rpm to 10,000 rpm, more preferably 1,000 rpm to 7,000 rpm.

A physiologically active substance immobilized on the surface for the biosensor of the present invention is not particularly limited, as long as it interacts with a measurement target. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanamycin antibody, anti-metamphetamine antibody, or antibodies against O antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

A biosensor to which a physiologically active substance is immobilized as described above can be used to detect and/or measure a substance which interacts with the physiologically active substance.

In the present invention, it is preferable to detect and/or measure an interaction between a physiologically active substance immobilized on the substrate for sensor and a test substance by a nonelectric chemical method. Examples of a non-electrochemical method may include a surface plasmon resonance (SPR) measurement technique, a quartz crystal microbalance (QCM) measurement technique, and a measurement technique that uses functional surfaces ranging from gold colloid particles to ultra-fine particles.

In a preferred embodiment of the present invention, the biosensor of the present invention can be used as a biosensor for surface plasmon resonance which is characterized in that it comprises a metal film placed on a transparent substrate.

A biosensor for surface plasmon resonance is a biosensor used for a surface plasmon resonance biosensor, meaning a member comprising a portion for transmitting and reflecting light emitted from the sensor and a portion for immobilizing a physiologically active substance. It may be fixed to the main body of the sensor or may be detachable.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light.

A device using a system known as the Kretschmann configuration is an example of a surface plasmon measurement device for analyzing the properties of a substance to be measured using a phenomenon whereby a surface plasmon is excited with a lightwave (for example, Japanese Patent Laid-Open No. 6-167443). The surface plasmon measurement device using the above system basically comprises a dielectric block formed in a prism state, a metal film that is formed on a face of the dielectric block and comes into contact with a measured substance such as a sample solution, a light source for generating a light beam, an optical system for allowing the above light beam to enter the dielectric block at various angles so that total reflection conditions can be obtained at the interface between the dielectric block and the metal film, and a light-detecting means for detecting the state of surface plasmon resonance, that is, the state of attenuated total reflection, by measuring the intensity of the light beam totally reflected at the above interface.

In order to achieve various incident angles as described above, a relatively thin light beam may be caused to enter the above interface while changing an incident angle. Otherwise, a relatively thick light beam may be caused to enter the above interface in a state of convergent light or divergent light, so that the light beam contains components that have entered therein at various angles. In the former case, the light beam whose reflection angle changes depending on the change of the incident angle of the entered light beam can be detected with a small photodetector moving in synchronization with the change of the above reflection angle, or it can also be detected with an area sensor extending along the direction in which the reflection angle is changed. In the latter case, the light beam can be detected with an area sensor extending to a direction capable of receiving all the light beams reflected at various reflection angles.

With regard to a surface plasmon measurement device with the above structure, if a light beam is allowed to enter the metal film at a specific incident angle greater than or equal to a total reflection angle, then an evanescent wave having an electric distribution appears in a measured substance that is in contact with the metal film, and a surface plasmon is excited by this evanescent wave at the interface between the metal film and the measured substance. When the wave vector of the evanescent light is the same as that of a surface plasmon and thus their wave numbers match, they are in a resonance state, and light energy transfers to the surface plasmon. Accordingly, the intensity of totally reflected light is sharply decreased at the interface between the dielectric block and the metal film. This decrease in light intensity is generally detected as a dark line by the above light-detecting means. The above resonance takes place only when the incident beam is p-polarized light. Accordingly, it is necessary to set the light beam in advance such that it enters as p-polarized light.

If the wave number of a surface plasmon is determined from an incident angle causing the attenuated total reflection (ATR), that is, an attenuated total reflection angle ($\theta$SP), the dielectric constant of a measured substance can be determined. As described in Japanese Patent Laid-Open No. 11-326194, a light-detecting means in the form of an array is considered to be used for the above type of surface plasmon measurement device in order to measure the attenuated total reflection angle ($\theta$SP) with high precision and in a large dynamic range. This light-detecting means comprises multiple photo acceptance units that are arranged in a certain direction, that is, a direction in which different photo acceptance units receive the components of light beams that are totally reflected at various reflection angles at the above interface.

In the above case, there is established a differentiating means for differentiating a photodetection signal outputted from each photo acceptance unit in the above array-form light-detecting means with regard to the direction in which the photo acceptance unit is arranged. An attenuated total reflection angle ($\theta$SP) is then specified based on the derivative value outputted from the differentiating means, so that properties associated with the refractive index of a measured substance are determined in many cases.

In addition, a leaking mode measurement device described in "Bunko Kenkyu (Spectral Studies)" Vol. 47, No. 1 (1998), pp. 21 to 23 and 26 to 27 has also been known as an example of measurement devices similar to the above-described device using attenuated total reflection (ATR). This leaking mode measurement device basically comprises a dielectric block formed in a prism state, a clad layer that is formed on a face of the dielectric block, a light wave guide layer that is formed on the clad layer and comes into contact with a sample solution, a light source for generating a light beam, an optical system for allowing the above light beam to enter the dielectric block at various angles so that total reflection conditions can be obtained at the interface between the dielectric block and the clad layer, and a light-detecting means for detecting the excitation state of waveguide mode, that is, the state of attenuated total reflection, by measuring the intensity of the light beam totally reflected at the above interface.

In the leaking mode measurement device with the above structure, if a light beam is caused to enter the clad layer via the dielectric block at an incident angle greater than or equal to a total reflection angle, only light having a specific wave number that has entered at a specific incident angle is transmitted in a waveguide mode into the light wave guide layer, after the light beam has penetrated the clad layer. Thus, when the waveguide mode is excited, almost all forms of incident light are taken into the light wave guide layer, and thereby the state of attenuated total reflection occurs, in which the intensity of the totally reflected light is sharply decreased at the above interface. Since the wave number of a waveguide light depends on the refractive index of a measured substance placed on the light wave guide layer, the refractive index of the measurement substance or the properties of the measured substance associated therewith can be analyzed by determining the above specific incident angle causing the attenuated total reflection.

In this leaking mode measurement device also, the above-described array-form light-detecting means can be used to detect the position of a dark line generated in a reflected light due to attenuated total reflection. In addition, the above-described differentiating means can also be applied in combination with the above means.

The above-described surface plasmon measurement device or leaking mode measurement device may be used in random screening to discover a specific substance binding to a desired sensing substance in the field of research for development of new drugs or the like. In this case, a sensing substance is immobilized as the above-described measured substance on the above thin film layer (which is a metal film in the case of a surface plasmon measurement device, and is a clad layer and a light guide wave layer in the case of a leaking mode measurement device), and a sample solution obtained by dissolving various types of test substance in a solvent is added to the sensing substance. Thereafter, the above-described attenuated total reflection angle ($\theta$SP) is measured periodically when a certain period of time has elapsed.

If the test substance contained in the sample solution is bound to the sensing substance, the refractive index of the sensing substance is changed by this binding over time. Accordingly, the above attenuated total reflection angle ($\theta$SP) is measured periodically after the elapse of a certain time, and it is determined whether or not a change has occurred in the above attenuated total reflection angle ($\theta$SP), so that a binding state between the test substance and the sensing substance is measured. Based on the results, it can be determined whether or not the test substance is a specific substance binding to the sensing substance. Examples of such a combination between a specific substance and a sensing substance may include an antigen and an antibody, and an antibody and an antibody. More specifically, a rabbit anti-human IgG antibody is immobilized as a sensing substance on the surface of a thin film layer, and a human IgG antibody is used as a specific substance.

It is to be noted that in order to measure a binding state between a test substance and a sensing substance, it is not always necessary to detect the angle itself of an attenuated total reflection angle ($\theta$SP). For example, a sample solution may be added to a sensing substance, and the amount of an attenuated total reflection angle ($\theta$SP) changed thereby may be measured, so that the binding state can be measured based on the magnitude by which the angle has changed. When the above-described array-form light-detecting means and differentiating means are applied to a measurement device using attenuated total reflection, the amount by which a derivative value has changed reflects the amount by which the attenuated total reflection angle ($\theta$SP) has changed. Accordingly, based on the amount by which the derivative value has changed, a binding state between a sensing substance and a test substance can be measured (Japanese Patent Application No. 2000-398309 filed by the present applicant). In a measuring method and a measurement device using such attenuated total reflection, a sample solution consisting of a solvent and a test substance is added dropwise to a cup- or petri dish-shaped measurement chip wherein a sensing substance is immobilized on a thin film layer previously formed at the bottom, and then, the above-described amount by which an attenuated total reflection angle (θSP) has changed is measured.

Moreover, Japanese Patent Laid-Open No. 2001-330560 describes a measurement device using attenuated total reflection, which involves successively measuring multiple measurement chips mounted on a turntable or the like, so as to measure many samples in a short time.

When the biosensor of the present invention is used in surface plasmon resonance analysis, it can be applied as a part of various surface plasmon measurement devices described above.

The present invention will be further specifically described in the following examples. However, the examples are not intended to limit the scope of the present invention.

EXAMPLES

Example A1

This Example relates to the production of sensor chips for immobilizing a protein.
(1) Preparation of Sample 1 (Comparative Example)
Biacore sensor chip CM-5 (research grade) was directly used as a surface bound with carboxymethyl dextran (Sample 1).
(2) Preparation of Sample 2 (Comparative Example)
(2-1) Preparation of Substrate Having OH Group
Biacore sensor chip Au was used as a surface comprising only a gold film formed on a sensor chip to perform an experiment. The sensor chip Au was treated with UV ozone for 12 minutes, then dipped in a mixture solution of ethanol/water (80/20) dissolving therein 5.0 mM 16-hydroxyhexadecanethiol (manufactured by Frontier Scientific), and incubated for 20 minutes in a shaking incubator set at 40° C., followed by washing five times with water, five times with 50 ml of ethanol/water (80/20), and five times with 50 ml of water.
(2-2) Treatment with Epichlorohydrin
The substrate was dipped in a mixture solution of 20 ml of 0.4 M sodium hydroxide, 20 ml of diethylene glycol dimethyl ether, and 2.0 ml of epichlorohydrin and reacted for 4 hours in a shaking incubator set at 25° C., followed by washing twice with 50 ml of ethanol and five times with 50 ml of water.
(2-3) Treatment with Dextran
The substrate was dipped in a mixture solution of 40.5 ml of water, 13.5 g of dextran (T500, Pharmacia), and 4.5 ml of 1 M sodium hydroxide and reacted for 20 hours in a shaking incubator set at 25° C., followed by washing 15 times with 50 ml of water at 50° C.
(2-4) Treatment with Bromoacetic Acid
The substrate was dipped in a mixture solution of 3.5 g of bromoacetic acid and 27 g of 2 M sodium hydroxide solution and reacted for 16 hours in a shaking incubator set at 28° C., followed by washing with water. The substrate was reacted again with a bromoacetic acid solution for 16 hours, followed by washing with water to obtain Sample 2.
(3) Preparation of Sample 3 (Present Invention)
(3-1) Preparation of Substrate Having Amino Group Biacore sensor chip Au was used as a surface comprising only a gold film formed on a sensor chip to perform an experiment. The sensor chip Au was treated with UV ozone for 12 minutes and then reacted at 40° C. for 1 hour in a solution of 8 mL of ethanol and 2 mL of ultrapure water dissolving therein 45 μmol 11-hydroxy-1-undecanethiol (manufactured by Aldrich) and 4 μmol 16-mercaptohexadecanoic acid (manufactured by Aldrich), followed by washing once with ethanol and once with ultrapure water. Onto the substrate, 100 μl of a mixture solution of EDC (0.4 M)/NHS (0.1 M) was added dropwise and reacted at room temperature for 15 minutes to thereby perform activation, followed by washing once with ultrapure water. Onto the substrate, 50 μl of 1,2-bis(aminoethoxy)ethane was added dropwise and reacted at room temperature for 1 hour, followed by washing once with ultrapure water.
(3-2) Active Esterification of CMD
CMD (manufactured by Meito Sangyo; molecular weight of 1,000,000) was dissolved at 0.5% by weight in ultrapure water, and then supplemented with a mixture solution of EDC (1-(3-dimethylaminopropyl)-3-ethylcarbodiimide) (0.4 M)/NHS (N-hydroxysuccinimide) (0.1 M) in a calculation amount that activated 2% of the carboxyl groups through the reaction of the whole amount of the mixture solution, followed by stirring at room temperature for 5 minutes.
(3-3) Binding of Active Esterified CMD to Substrate
Onto the substrate prepared in the paragraph (3-1), 200 μl of the active esterified CMD solution prepared in the paragraph (3-2) was added dropwise and spin-coated at 7000 rpm for 45 seconds to thereby form a thin film of the active esterified carboxymethyl dextran on the substrate having an amino group. After reaction at room temperature for 1 hour, the substrate was washed once with 0.1 N NaOH and once with ultrapure water to obtain Sample 3.

Example A2

This Example relates to the immobilization of a protein on the sensor chips obtained in Example A1. CA (carbonic anhydrase; manufactured by SIGMA) was used as the protein. The CA used was confirmed to have an isoelectric point of approximately 5.8 from comparison with a marker (Broad pI Kit, pH 3.5 to 9.3; manufactured by Amersham Biosciences) measured simultaneously therewith in an electrophoresis experiment using AE-8150 (manufactured by ATTO). 10 μl of a solution of 1 mg of CA dissolved in 1 ml of HBS-EP buffer (manufactured by Biacore, 0.01 M HEPES (pH 7.4), 0.15 M NaCl, 0.005% Surfactant P20, 3 mM EDTA) was weighed and supplemented with 90 μl of acetic acid buffer (manufactured by Biacore, pH 5.0) to thereby adjust the CA solution to 0.1 mg/ml (pH 5.0, 0.1 mg/ml).

The Samples 1 to 3 prepared in Example A1 were loaded onto a surface plasmon resonance apparatus Biacore 3000 manufactured by Biacore, which was in turn perfused with each of an aqueous solution containing 0.4 M EDC and 0.1 M NHS, the CA solution (pH 5.0, 0.1 mg/ml), and an ethanol amine solution (Biacore) for 5 minutes and then with 10 mM NaOH for 1 minute×2 runs to thereby investigate immobilization. A HBS-N buffer (manufactured by Biacore, 0.01 M HEPES (pH 7.4), 0.15 M NaCl) was used as a running buffer. The obtained sensorgram is shown in FIG. 1.

The respective amounts of CA immobilization were 7757 RU (Sample 1), 16487 RU (Sample 2), and 35309 RU (Sample 3). It was demonstrated that a CMD-bound surface having a larger amount of immobilization of a protein than those of a commercially available CMD-bound surface and a CMD-bound surface produced by the conventional production method can be produced conveniently by the present invention.

Example A3

Figure 2:
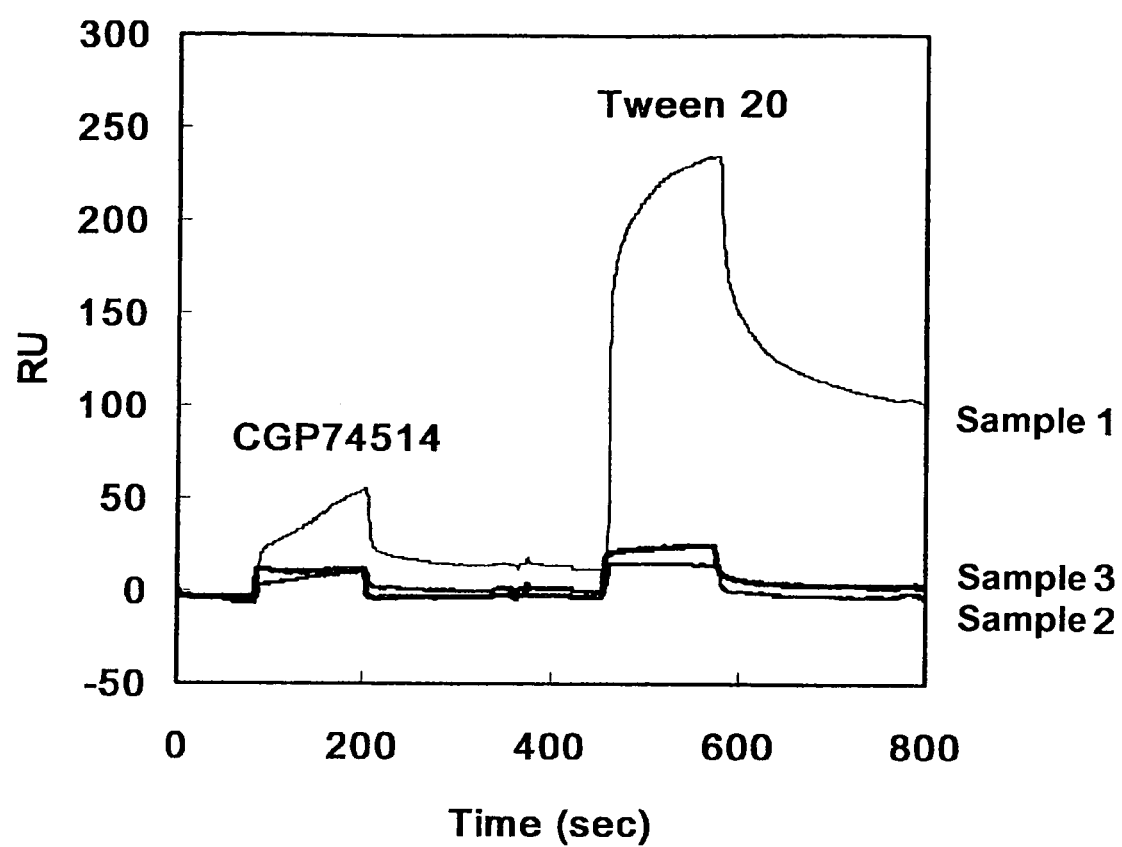
FIG. 2 is a sensorgram showing the nonspecific adsorption of a low-molecular compound on the sensor chips obtained in Example A1.

This Example relates to the nonspecific adsorption of a low-molecular compound on the sensor chips obtained in Example 1. CGP74514 as an inhibitor for cyclin-dependent kinases and Tween 20 as a surfactant were selected as the low-molecular compounds to investigate the ability to suppress the nonspecific adsorption onto the sensor chip surfaces. A sensorgram obtained by perfusing CGP74514 (50 µM) for 2 minutes and then Tween 20 (0.005 wt %) for 2 minutes into each sample is shown in FIG. 2.

CGP74514 and Tween 20 were nonspecifically adsorbed on the Sample 1, which was a commercially available CMD-bound surface, whereas the nonspecific adsorption of both CGP74514 and Tween 20 was hardly observed for the Samples 2 and 3. This demonstrated that a CMD-bound surface having more excellent ability to suppress the nonspecific adsorption of a low-molecular compound than that of a commercially available CMD-bound surface can be produced conveniently by the present approach.

Example A4

This Example relates to the production of sensor chips at varying concentrations of CMD for spin coating.
(1) Preparation of Sample 4 (Example)
Sample 4 was obtained by the same procedures as in the preparation of the Sample 3 except that a CMD concentration was changed to 0.2%.
(2) Preparation of Sample 5 (Example)
Sample 5 was obtained by the same procedures as in the preparation of the Sample 3 except that a CMD concentration was changed to 0.1%.
(3) Preparation of Sample 6 (Example)
Sample 6 was obtained by the same procedures as in the preparation of the Sample 3 except that a CMD concentration was changed to 0.08%.
(4) Preparation of Sample 7 (Example)
Sample 7 was obtained by the same procedures as in the preparation of the Sample 3 except that a CMD concentration was changed to 0.05%.
(5) Preparation of Sample 8 (Example)
Sample 8 was obtained by the same procedures as in the preparation of the Sample 3 except that a CMD concentration was changed to 0.02%.

Example A5

This Example relates to the preconcentration of a protein on the sensor chips obtained in Examples A1 and A4. BSA (bovine serum albumin; manufactured by SIGMA) was used as the protein. The BSA used was confirmed to have an isoelectric point of approximately 6.1 from comparison with a marker (Broad pI Kit, pH 3.5 to 9.3; manufactured by Amersham Biosciences) measured simultaneously therewith in an electrophoresis experiment using AE-8150 (manufactured by ATTO). 10 µl of a solution of 1 mg of BSA dissolved in 1 ml of HBS-EP buffer (manufactured by Biacore, pH 7.4) was weighed, and supplemented with 90 µl of acetic acid buffer (manufactured by Biacore, pH 5.0) to thereby adjust the BSA solution to 0.1 mg/ml (pH 5.0, 0.1 mg/ml).
The Samples 1 to 8 prepared in Examples A1 and A4 were loaded onto a surface plasmon resonance apparatus Biacore 3000 manufactured by Biacore, which was in turn perfused with the BSA solution (pH 5.0, 0.1 mg/ml) for 5 minutes to thereby investigate preconcentration. The obtained results are summarized in Table 1.

TABLE 1

Preconcentration of BSA on CMD-bound surface

| Sample name | CMD concentration for spin coating | BSA pre-concentration | Remarks |
| --- | --- | --- | --- |
| Sample 1 | — | 22101 RU | Comparative Example |
| Sample 2 | — | 38892 RU | Comparative Example |
| Sample 3 | 0.5% | 72893 RU | Present invention |
| Sample 4 | 0.2% | 60105 RU | Present invention |
| Sample 5 | 0.1% | 43337 RU | Present invention |
| Sample 6 | 0.08% | 31765 RU | Present invention |
| Sample 7 | 0.05% | 18793 RU | Present invention |
| Sample 8 | 0.02% | 4356 RU | Present invention |

It was demonstrated that the amount of preconcentration of a protein can be controlled by controlling the concentration of an active esterified CMD solution for spin coating. It is considered that a higher concentration of an active esterified CMD solution from which a spin-coating thin film is obtained increases more the amount of CMD immobilized on a substrate surface, thereby resulting in an increased amount of preconcentration of a protein.

Example A6

This Example relates to the binding of a polymer containing a carboxyl group other than CMD to a substrate surface.
(1) Preparation of Sample 9 (Example)
Sample 9 was obtained by the same procedures as in the preparation of the Sample 3 except that a polymer was changed from CMD to sodium alginate 500 to 600 (Wako Pure Chemical Industries, Ltd.).

Example A7

Figure 3:
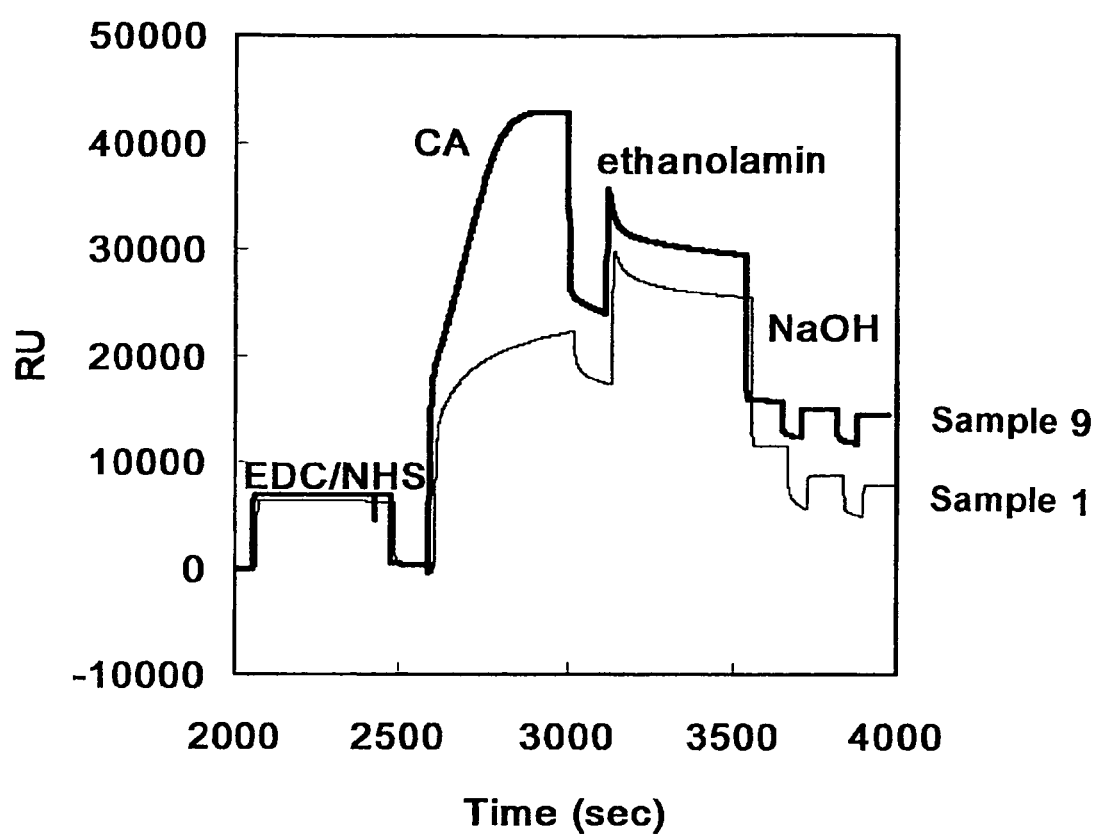
FIG. 3 is a sensorgram showing the preconcentration of a protein on sensor chips obtained in Examples A1 and A6.

This Example relates to the preconcentration of a protein on the sensor chips obtained in Examples A1 and A6. CA was used as the protein to investigate the immobilization of CA by the same procedures as in Example A2. The results are shown in FIG. 3.

When the protein was bound to the substrate surface bound with active esterified sodium alginate, the substrate surface had the ability to immobilize the protein thereon equal to or higher than that of the commercially available CMD-bound surface. Therefore, it was demonstrated that the present invention is also effective for the binding of a polymer containing a carboxyl group other than CMD to a substrate surface.

Example A8

Figure 4:
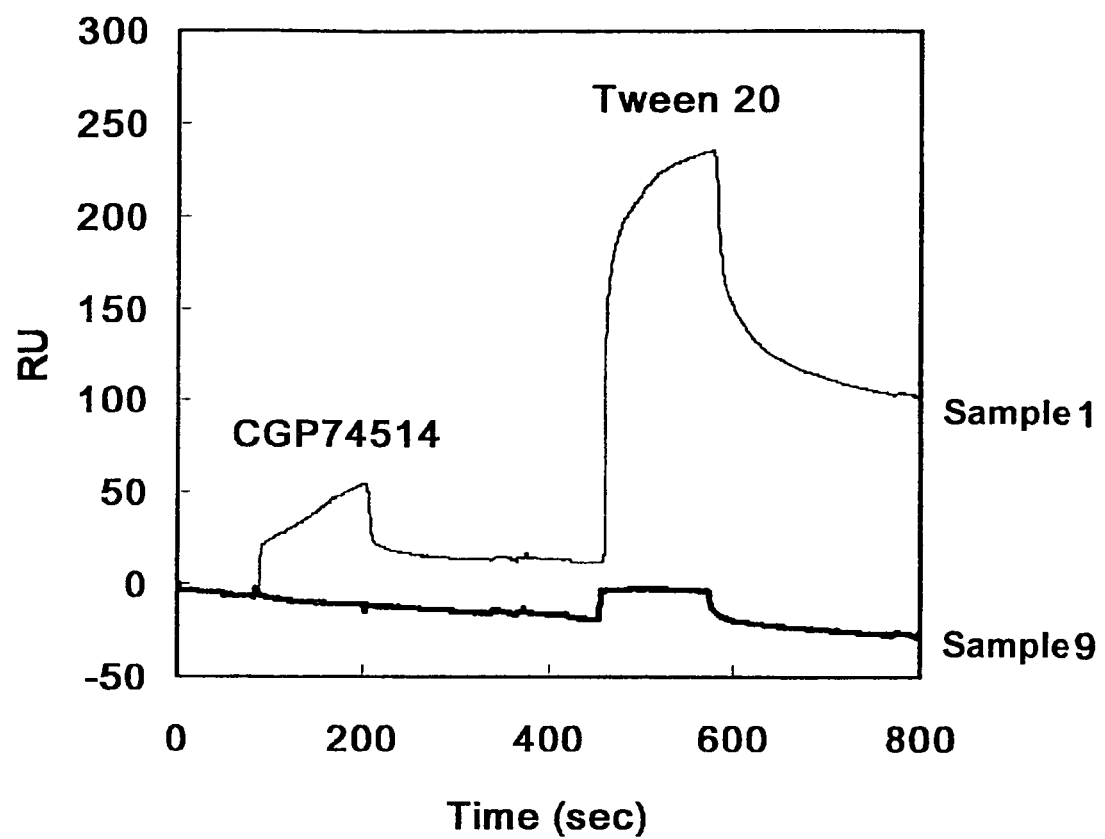
FIG. 4 is a sensorgram showing the nonspecific adsorption of a low-molecular compound on the sensor chips obtained in Examples A1 and A6.

This Example relates to the nonspecific adsorption of a low-molecular compound on the sensor chips obtained in Examples A1 and A6. The ability to suppress the nonspecific adsorption of low-molecular compounds CGP74514 and Tween 20 onto the sensor chip surfaces was investigated by the same procedures as in Example A3. The obtained sensorgram is shown in FIG. 4.

The Sample 9 prepared on the basis of the present invention as in Example 3 had more excellent ability to suppress the nonspecific adsorption of the low-molecular compounds than that of the Sample 1, which was a commercially available CMD-bound surface. Therefore, it was demonstrated that a surface having more excellent ability to suppress the nonspecific adsorption of a low molecule than that of a commercially available CMD-bound surface can be produced conveniently even when a polymer containing a carboxyl group other than CMD is used.

Example A9

A hydrogel film capable of immobilizing a protein thereon was produced by use of a highly water-soluble SAM compound to evaluate the amount of immobilization of a protein and nonspecific adsorption performance.
(1) Preparation of Substrate
A mixture aqueous solution (4.995 mM 6-hydroxy-1-undecanethiol/0.005 mM 8-amino-1-octanethiol, hydrochloride) of 6-hydroxy-1-undecanethiol (manufactured by Aldrich) and 8-amino-1-octanethiol, hydrochloride (manufactured by Dojindo Laboratories) was prepared. This solution was designated as Solution A.

Next, a gold thin film was formed by a method described below on the upper surface of a plastic prism obtained by injection-molding ZEONEX (manufactured by Zeon Corp). The prism was secured to a substrate holder of a sputtering apparatus, and a vacuum (base pressure of 1×10-3 Pa or less) was drawn therein. Thereafter, Ar gas was introduced (1 Pa) to the apparatus, and RF power (0.5 kW) was applied to the substrate holder for approximately 9 minutes with the substrate holder rotated (20 rpm) to plasma-treat the prism surface. Next, Ar gas was stopped, and a vacuum was drawn therein. Ar gas was introduced (0.5 Pa) again to the apparatus, and DC power (0.2 kW) was applied to a 8-inch Cr target for approximately 30 seconds with the substrate holder rotated (10 to 40 rpm) to draw a 2-nm Cr thin film thereon. Subsequently, Ar gas was stopped, and a vacuum was drawn again. Ar gas was introduced (0.5 Pa) again to the apparatus, and DC power (1 kW) was applied to a 8-inch Au target for approximately 50 seconds with the substrate holder rotated (20 rpm) to draw an approximately 50-nm Au thin film thereon.

The above-obtained sensor stick on which the Au thin film was drawn was dipped in the Solution A at 40° C. for 1 hour and washed ten times with ultrapure water.
(2) Active Esterification of CMD (Carboxymethyl Dextran)
After the dissolution of 4.95 ml of a solution of 0.1% by weight of CMD (manufactured by Meito Sangyo; molecular weight of 1,000,000), a mixture solution of EDC (1-Ethyl-3-[3-dimethylaminopropyl]carbodiimide hydrochloride) (0.4 M)/NHS (N-hydroxysulfosuccinimide) (0.1 M) was added thereto in a calculation amount (50 µl) that activated 2% of the carboxyl groups through the reaction of the whole amount of the mixture solution, followed by stirring at room temperature.
(3) Binding Reaction of CMD to Substrate
Onto the substrate prepared in the paragraph (1), 500 µl of the active esterified CMD solution prepared in the paragraph (2) was added dropwise and spin-coated at 1000 rpm for 45 seconds to thereby form a thin film of the active esterified carboxymethyl dextran on the substrate having an amino group. After reaction at room temperature for 1 hour, the substrate was washed five times with 0.1 N NaOH and five times with ultrapure water to obtain Sample 1.

Example A10

Example A10 relates to the immobilization of a protein on the sensor sample obtained in Example A9. CA (carbonic anhydrase; manufactured by SIGMA) was used as the protein.

The Sample 1 prepared in Example A9 was loaded onto a surface plasmon resonance apparatus. A PBS buffer was injected thereto, and a base line was confirmed (the resonance angle here was used as a reference point). Then, the injection of an aqueous solution containing 0.2 M EDC (1-(3-dimethylaminopropyl)-3-ethylcarbodiimide) and 50 mM NHS (N-hydroxysuccinimide) and 7-minute standing, next the injection of a PBS buffer and 1-minute standing, next the injection of 0.1 mg/ml CA solution (acetic acid buffer, pH 5.0) and 15-minute standing, next the injection of a PBS buffer and 1-minute standing, next the injection of 1 M ethanol amine solution (Biacore) and 7-minute standing, next the injection of a PBS buffer and 1-minute standing, next three runs of the injection of 10 mM NaOH and 1-minute standing, and finally the injection of a PBS buffer and 1-minute standing were performed. The difference between the resonance angle here and the original resonance angle was used as the amount of CA immobilization. In this context, a resonance angle of 1/10000 degrees is referred to as 1 RU.

The amount of CA immobilization was 5200 RU. It was shown that a large amount of proteins can be immobilized even on a surface prepared with a highly water-soluble SAM compound.

Example A11

Example A11 relates to the nonspecific adsorption of a low-molecular compound on the sensor sample obtained in Example A9. CGP74514 as an inhibitor for cyclin-dependent kinases and Tween 20 as a surfactant were selected as the low-molecular compounds to investigate the ability to suppress the nonspecific adsorption onto the sensor sample surface.

The Sample 1 prepared in Example 9 was loaded onto a surface plasmon resonance apparatus. A PBS buffer was injected thereto, and a base line was confirmed (the resonance angle here was used as a reference point). Then, the injection of a PBS buffer solution of CGP74514 (50 µM) or a PBS buffer solution of Tween 20 (0.005% by weight) and 2-minute standing and finally the injection of a PBS buffer and 2-minute standing were performed. The difference between the resonance angle here and the original resonance angle was used as the amount of nonspecific adsorption.

The amounts of nonspecific adsorption on the Sample 1 were 3 RU (CGP74514) and 5 RU (Tween 20). It was shown that the nonspecific adsorption of a low-molecular compound can be suppressed even on a surface prepared with a highly water-soluble SAM compound.

Example A12

A hydrogel film capable of immobilizing a protein thereon was produced by use of a highly water-soluble SAM compound to evaluate the amount of immobilization of a protein.
(1) Preparation of Substrate
1 mM aqueous solution of 6-amino-1-hexanethiol, hydrochloride (manufactured by Dojindo Laboratories) was prepared. This solution was designated as Solution A.

Next, a gold thin film was formed by a method described below on the upper surface of a plastic prism obtained by injection-molding ZEONEX (manufactured by Zeon Corp). The prism was secured to a substrate holder of a sputtering apparatus, and a vacuum (base pressure of 1×10-3 Pa or less) was drawn therein. Thereafter, Ar gas was introduced (1 Pa) to the apparatus, and RF power (0.5 kW) was applied to the substrate holder for approximately 9 minutes with the substrate holder rotated (20 rpm) to plasma-treat the prism surface. Next, Ar gas was stopped, and a vacuum was drawn therein. Ar gas was introduced (0.5 Pa) again to the apparatus, and DC power (0.2 kW) was applied to a 8-inch Cr target for approximately 30 seconds with the substrate holder rotated (10 to 40 rpm) to draw a 2-nm Cr thin film thereon. Subsequently, Ar gas was stopped, and a vacuum was drawn again. Ar gas was introduced (0.5 Pa) again to the apparatus, and DC power (1 kW) was applied to a 8-inch Au target for approximately 50 seconds with the substrate holder rotated (20 rpm) to draw an approximately 50-nm Au thin film thereon.

The above-obtained sensor stick on which the Au thin film was drawn was dipped in the Solution A at 40° C. for 1 hour and washed five times with ultrapure water.

(2) Active Esterification of CMD (Carboxymethyl Dextran)

After the dissolution of 10 g of a solution of 1% by weight of CMD (manufactured by Meito Sangyo; molecular weight of 1,000,000, substitution degree of 0.65) (amount of carboxyl group: $3.3 \times 10^{-2}$ mol), 10 ml of a mixed aqueous solution of EDC (1-Ethyl-3-[3-dimethylaminopropyl]carbodiimide hydrochloride which is a carbodiimide derivative) (the amount is shown in Table 2), and the nitrogen-containing compound having a hydroxyl group (the type and the amount is shown in Table 2) (NHS (N-Hydroxysuccinimide) or HOBt (1-Hydroxybenzotriazole)) was added thereto, followed by stirring 1 hour at room temperature.

(3) Binding Reaction of CMD to Substrate

Onto the substrate prepared in the paragraph (1), 1 ml of the active esterified CMD solution prepared in the paragraph (2) was added dropwise and spin-coated at 1000 rpm for 45 seconds to thereby form a thin film of the active esterified carboxymethyl dextran on the substrate having an amino group. After reaction at room temperature for 15 minutes, the substrate was immersed in 1N NaOH for 30 minutes, and washed 5 times with ultrapure water to obtain Sample 1-A to 8-A.

Further, at 65 minutes (B), 70 minutes (C), 75 minutes (D) and 80 minutes (E) after the start of active esterification reaction, the spin coating was carried out in the same way as mentioned above, so as to obtain Samples 1-B to 8-B, Samples 1-C to 8-C, Samples 1-D to 8-D, and Samples 1-E to 8-E.

Comparative Example A3

(i) Preparation of Substrate Having OH Group 5 mM solution of 16-hydroxy-1-hexadecanethiol (manufactured by Frontier Scientific) in (ethanol/water=8/2) was prepared. This solution is refereed to as Solution B. Next, a gold film of 50 nm was formed on a sensor stick in the same way as in Example A12. The substrate was immersed in Solution B at 40□ for 60 minutes, followed by washing five times with ethanol, once with 50 ml of ethanol/water (80/20), and five times with 50 ml of ultrapure water.

(ii) Treatment with Epichlorohydrin

The substrate was dipped in a mixture solution of 20 ml of 0.4 M sodium hydroxide, 20 ml of diethylene glycol dimethyl ether, and 2.0 ml of epichlorohydrin and reacted for 4 hours in a shaking incubator set at 25° C., followed by washing twice with 50 ml of ethanol and five times with 50 ml of water.

(iii) Treatment with Dextran

The substrate was dipped in a mixture solution of 40.5 ml of water, 13.5 g of dextran (T500, Pharmacia), and 4.5 ml of 1 M sodium hydroxide and reacted for 20 hours in a shaking incubator set at 25° C., followed by washing 15 times with 50 ml of water at 50° C.

(iv) Treatment with Bromoacetic Acid

The substrate was dipped in a mixture solution of 3.5 g of bromoacetic acid and 27 g of 2 M sodium hydroxide solution and reacted for 16 hours in a shaking incubator set at 28° C., followed by washing with water. The substrate was reacted again with a bromoacetic acid solution for 16 hours, followed by washing with water to obtain Sample 9.

Example A13

Example A13 relates to the immobilization of a protein on the sensor sample obtained in Example A12 and Comparative Example A3. CA (carbonic anhydrase; manufactured by SIGMA) was used as the protein.

The Samples 1 to 9 prepared in Example A12 and Comparative Example A3 were loaded onto a surface plasmon resonance apparatus. A PBS buffer was injected thereto, and a base line was confirmed (the resonance angle here was used as a reference point). Then, the injection of an aqueous solution containing 0.2 M EDC (1-(3-dimethylaminopropyl)-3-ethylcarbodiimide) and 50 mM NHS (N-hydroxysuccinimide) and 7-minute standing, next the injection of a PBS buffer and 1-minute standing, next the injection of 0.1 mg/ml CA solution (acetic acid buffer, pH 5.0) and 15-minute standing, next the injection of a PBS buffer and 1-minute standing, next the injection of 1 M ethanol amine solution (Biacore) and 7-minute standing, next the injection of a PBS buffer and 1-minute standing, next three runs of the injection of 10 mM NaOH and 1-minute standing, and finally the injection of a PBS buffer and 1-minute standing were performed. The difference between the resonance angle here and the original resonance angle was used as the amount of CA immobilization. In this context, the difference of the resonance angle per DMSO 1% is referred to as 1500 RV.

The mean CA immobilization amount and the CV value (Coefficient of Variation: %) of A to E in Samples 1-8, and the CA immobilization amount in Sample 9 are shown in the following table. It was found that, on the surface of the present invention, many amount of protein can be immobilized by a simple method. The CV value means Coefficient of Variation, and represents a value obtained by dividing the standard deviation (square root of variance) by average. The smaller CV value means the smaller dispersion, which is preferred.

TABLE

Mean CA immobilization amount and CV value of A to E in Samples 1-8, and CA immobilization amount in Sample 9

| Sample No | EDC ($10^{-5}$ mol) | NHS ($10^{-6}$ mol) | HOBt ($10^{-7}$ mol) | CA(mean) Immobilization Amount(RV) | CA immobilization Amount: CV value(%) | Remark |
|---|---|---|---|---|---|---|
| 1 | 2 | 5 | — | 5200 | 5.5 | Invention |
| 2 | 4 | 10 | — | 8400 | 10.2 | Invention |
| 3 | 10 | 25 | — | 10500 | 10.5 | Invention |
| 4 | 20 | 50 | — | 15600 | 5.2 | Invention |
| 5 | 2 | — | 1.4 | 7100 | 1.7 | Invention |
| 6 | 6 | — | 2.8 | 12800 | 2.2 | Invention |
| 7 | 10 | — | 7 | 23400 | 2.7 | Invention |
| 8 | 20 | — | 14 | 24800 | 1.5 | Invention |
| 9 | — | — | — | 5200 | — | Comparative |

Example B1

This Example relates to the difference between reactions in a solution state and in a spin-coating thin film state in the production of a surface bound with CMD (carboxymethyl dextran).

(1) Preparation of Substrate Having Amino Group

Biacore sensor chip Au was used as a surface comprising only a gold film formed on a sensor chip to perform an experiment. The sensor chip Au was treated with UV ozone for 12 minutes and then reacted at 40° C. for 1 hour in a solution of 8 mL of ethanol and 2 mL of ultrapure water dissolving therein 45 μmol 11-hydroxy-1-undecanethiol (manufactured by Aldrich) and 4 μmol 16-mercaptohexadecanoic acid (manufactured by Aldrich), followed by washing once with ethanol and once with ultrapure water. Onto the substrate, 100 μl of a mixture solution of EDC (0.4 M)/NHS (0.1 M) was added dropwise and reacted at room temperature for 15 minutes to thereby perform activation, followed by washing once with ultrapure water. Onto the substrate, 50 μl of 1,2-bis(aminoethoxy)ethane was added dropwise and reacted at room temperature for 1 hour, followed by washing once with ultrapure water.

(2) Active Esterification of CMD

CMD (manufactured by Meito Sangyo; molecular weight of 1,000,000) was dissolved at 0.5% by weight in ultrapure water and then supplemented with a mixture solution of EDC (0.4 M)/NHS (0.1 M) in a calculation amount that activated 2% of the carboxyl groups through the reaction of the whole amount of the mixture solution, followed by stirring at room temperature for 5 minutes.

(3) Preparation of Sample 1 (Comparative Example)

Onto the substrate prepared in the paragraph (1), 200 μl of the active esterified CMD solution prepared in the paragraph (2) was added dropwise and reacted at room temperature for 1 hour, followed by washing once with 0.1 N NaOH and once with ultrapure water to obtain the surface of interest.

(4) Preparation of Sample 2 (Present Invention)

Onto the substrate prepared in the paragraph (1), 200 μl of the active esterified CMD solution prepared in the paragraph (2) was added dropwise and spin-coated at 7000 rpm for 45 seconds to thereby form a thin film of the active esterified carboxymethyl dextran on the substrate having an amino group. After reaction at room temperature for 1 hour, the substrate was washed once with 0.1 N NaOH and once with ultrapure water to obtain the surface of interest.

Example B2

This Example relates to the preconcentration of a protein on the sensor chips obtained in Example B1. BSA (bovine serum albumin; manufactured by SIGMA) was used as the protein. The BSA used was confirmed to have an isoelectric point of approximately 6.1 from comparison with a marker (Broad pI Kit, pH 3.5 to 9.3; manufactured by Amersham Biosciences) measured simultaneously therewith in an electrophoresis experiment using AE-8150 (manufactured by ATTO). 10 μl of a solution of 1 mg of BSA dissolved in 1 ml of HBS-EP buffer (manufactured by Biacore, 0.01 M HEPES (pH 7.4), 0.15 M NaCl, 0.005% Surfactant P20, 3 mM EDTA) was weighed and supplemented with 90 μl of acetic acid buffer (manufactured by Biacore, pH 5.0) to thereby adjust the BSA solution to 0.1 mg/ml (pH 5.0, 0.1 mg/ml).

The Samples 1 and 2 prepared in Example B1 were loaded onto a surface plasmon resonance apparatus Biacore 3000 manufactured by Biacore, which was in turn perfused with the BSA solution (pH 5.0, 0.1 mg/ml) for 5 minutes to thereby investigate preconcentration. The obtained results are summarized in Table 2.

TABLE 2

Preconcentration of BSA on CMD-bound surface

| Sample name | CMD binding method | BSA pre-concentration | Remarks |
|---|---|---|---|
| Sample 1 | Solution | 8309 RU | Comparative Example |
| Sample 2 | Spin-coating thin film | 73228 RU | Present invention |

The Sample 2 obtained by reacting the surface having an amino group with the active esterified CMD in a spin-coating thin film state had approximately 9 times the amount of preconcentration of BSA of the Sample 1 obtained by reacting the surface having an amino group with the active esterified CMD in a solution state. Therefore, it was demonstrated that the reaction of a hydrophilic polymer having a reactive group in a thin film state with a substrate surface is exceedingly effective in the production of a surface for immobilizing a physiologically active substance. Since a water-soluble polymer is present with a thread ball-like structure in water, the number of reactive groups capable of approaching a substrate surface is restricted due to its own excluded volume effect, with the result that the amount of the polymer bound to the substrate surface is restricted. By contrast, in a polymer in a spin-coating thin film state, it is considered that the number of reactive groups capable of approaching a substrate surface is increased by water evaporation to thereby increase the amount of the polymer immobilized on the substrate surface, with the result that the amount of preconcentration of a protein is increased.

Example B3

This Example relates to a method for producing a surface bound with a hydrophilic polymer having a reactive group other than active esterified CMD.
(1) Preparation of Sample 3 (Comparative Example)

Onto the substrate prepared in the paragraph (1) of Example B1, 200 µl of 10% P-30 solution was added dropwise and reacted at room temperature for 1 hour, followed by washing once with 0.1 N NaOH and once with ultrapure water to obtain Sample 3.
(2) Preparation of Sample 4 (Present Invention)

Onto the substrate prepared in the paragraph (1) of Example B1, 200 µl of 10% P-30 solution was added dropwise and spin-coated at 7000 rpm for 45 seconds to thereby form a thin film of the active esterified carboxymethyl dextran on the substrate having an amino group. After reaction at room temperature for 1 hour, the substrate was washed once with 0.1 N NaOH and once with ultrapure water to obtain Sample 4.

Example B4

This Example relates to the preconcentration of a protein on the sensor chips obtained in Example B3. The preconcentration of BSA was investigated by totally the same procedures as in Example 2. The obtained results are summarized in Table 3.

TABLE 3

Preconcentration of BSA on P30-bound surface

| Sample name | P30 binding method | BSA pre-concentration | Remarks |
|---|---|---|---|
| Sample 3 | Solution | 1089 RU | Comparative Example |
| Sample 4 | Spin-coating thin film | 2507 RU | Present invention |

The Sample 4 obtained by reacting the surface having an amino group with the active esterified P-30 in a spin-coating thin film state had approximately 2.5 times the amount of preconcentration of BSA of the Sample 3 obtained by reacting the surface having an amino group with the active esterified P-30 in a solution state. Therefore, it was demonstrated that the reaction of a hydrophilic polymer having a reactive group in a thin film state with a substrate surface is exceedingly important for the production of a surface for immobilizing a physiologically active substance.

Example B5

This Example relates to the production of a CMD-bound surface by a conventional method.
(1) Preparation of Sample 5 (Comparative Example)

Biacore sensor chip CM-5 (research grade) was directly used as a surface bound with carboxymethyl dextran (Sample 5).
(2) Preparation of Sample 6 (Comparative Example)
(i) Preparation of Substrate Having OH Group Biacore sensor chip Au was used as a surface comprising only a gold film formed on a sensor chip to perform an experiment. The sensor chip Au was treated with UV ozone for 12 minutes, then dipped in a mixture solution of ethanol/water (80/20) dissolving therein 5.0 mM 16-hydroxyhexadecanethiol (manufactured by Frontier Scientific), and incubated for 20 minutes in a shaking incubator set at 40° C., followed by washing five times with water, five times with 50 ml of ethanol/water (80/20), and five times with 50 ml of water.
(ii) Treatment with Epichlorohydrin The substrate was dipped in a mixture solution of 20 ml of 0.4 M sodium hydroxide, 20 ml of diethylene glycol dimethyl ether and 2.0 ml of epichlorohydrin, and reacted for 4 hours in a shaking incubator set at 25° C., followed by washing twice with 50 ml of ethanol and five times with 50 ml of water.
(iii) Treatment with Dextran The substrate was dipped in a mixture solution of 40.5 ml of water, 13.5 g of dextran (T500, Pharmacia), and 4.5 ml of 1 M sodium hydroxide and reacted for 20 hours in a shaking incubator set at 25° C., followed by washing 15 times with 50 ml of water at 50° C.
(iv) Treatment with Bromoacetic Acid The substrate was dipped in a mixture solution of 3.5 g of bromoacetic acid and 27 g of 2 M sodium hydroxide solution and reacted for 16 hours in a shaking incubator set at 28° C., followed by washing with water. The substrate was reacted again with a bromoacetic acid solution for 16 hours, followed by washing with water to obtain Sample 6.

Example B6

This Example relates to the immobilization of a protein on the sensor chips obtained in Examples B1 and B5. CA (carbonic anhydrase; manufactured by SIGMA) was used as the protein. The CA used was confirmed to have an isoelectric point of approximately 5.8 from comparison with a marker (Broad pI Kit, pH 3.5 to 9.3; manufactured by Amersham Biosciences) measured simultaneously therewith in an electrophoresis experiment using AE-8150 (manufactured by ATTO). 10 µl of a solution of 1 mg of CA dissolved in 1 ml of HBS-EP buffer (manufactured by Biacore, 0.01 M HEPES (pH 7.4), 0.15 M NaCl, 0.005% Surfactant P20, 3 mM EDTA) was weighed and supplemented with 90 µl of acetic acid buffer (manufactured by Biacore, pH 5.0) to thereby adjust the CA solution to 0.1 mg/ml (pH 5.0, 0.1 mg/ml).

Figure 5:
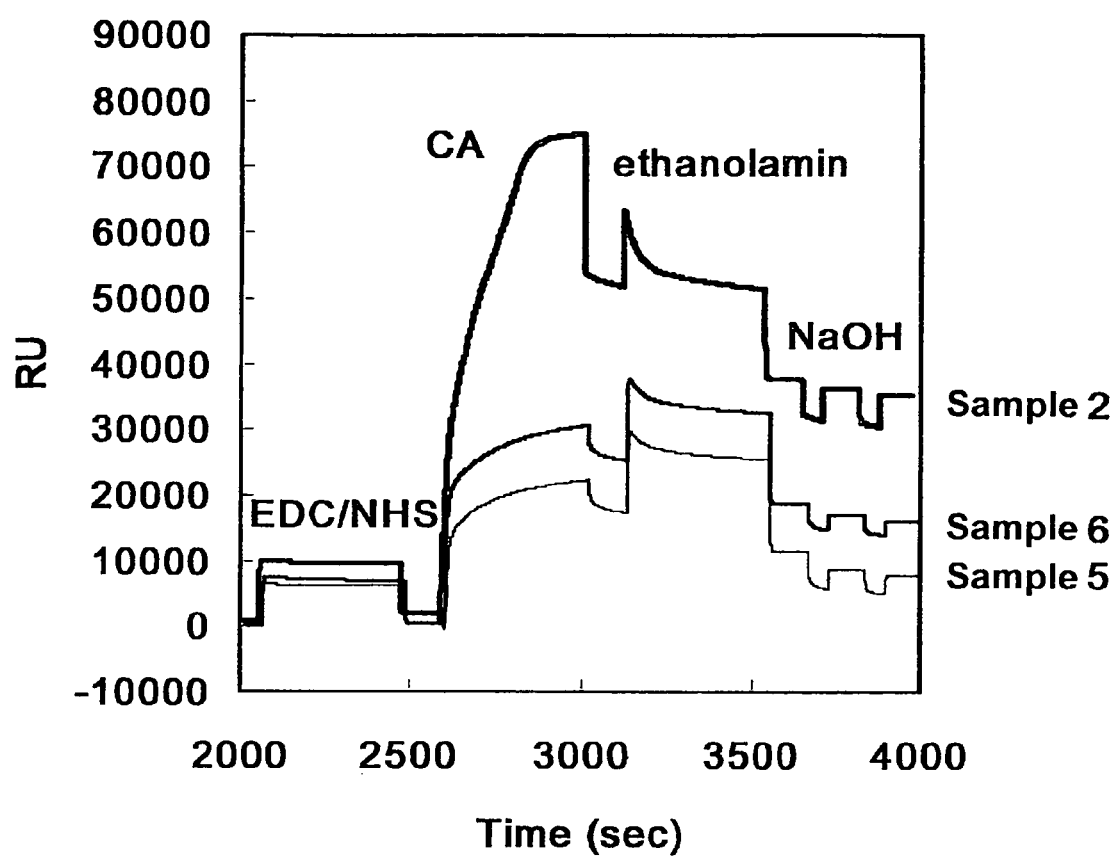
FIG. 5 is a sensorgram showing the immobilization of a protein on sensor chips obtained in Examples B1 and B5.

The Samples 2, 5, and 6 prepared in Examples B1 and B5 were loaded onto a surface plasmon resonance apparatus Biacore 3000 manufactured by Biacore, which was in turn perfused with each of an aqueous solution containing 0.4 M EDC (1-(3-dimethylaminopropyl)-3-ethylcarbodiimide) and 0.1 M NHS (N-hydroxysuccinimide), the CA solution (pH 5.0, 0.1 mg/ml), and an ethanol amine solution (Biacore) for 5 minutes and then with 10 mM NaOH for 1 minute×2 runs to thereby investigate immobilization. A HBS-N buffer (manufactured by Biacore, 0.01 M HEPES (pH 7.4), 0.15 M NaCl) was used as a running buffer. The obtained sensorgram is shown in FIG. 5.

The respective amounts of CA immobilization were 35309 RU (Sample 2), 7757 RU (Sample 5), and 16487 RU (Sample 6). It was demonstrated that a CMD-bound surface having a larger amount of immobilization of a protein than those of a commercially available CMD-bound surface and a CMD-bound surface produced by the conventional production method can be produced conveniently by the present invention.

Example B6

Figure 6:
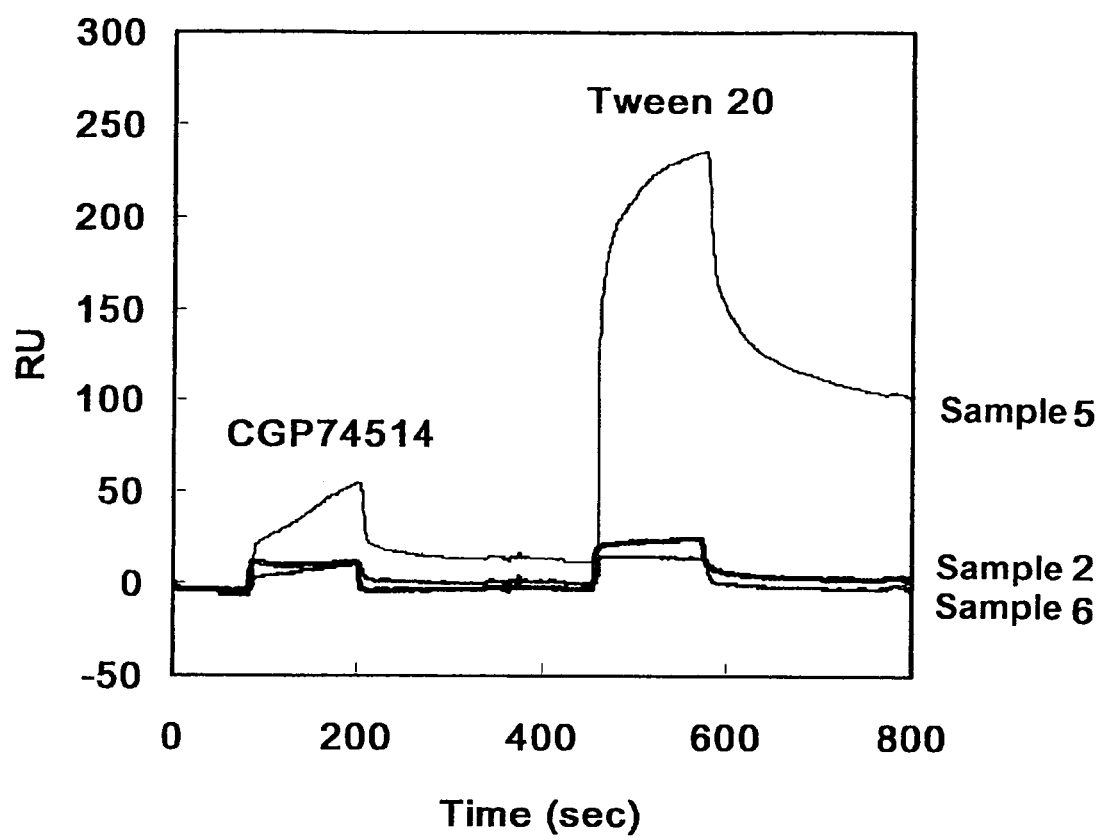
FIG. 6 is a sensorgram showing the nonspecific adsorption of a low-molecular compound on the sensor chips obtained in Examples B1 and B5.

This Example relates to the nonspecific adsorption of a low-molecular compound on the sensor chips obtained in Examples B1 and B5. CGP74514 as an inhibitor for cyclin-dependent kinases and Tween 20 as a surfactant were selected as the low-molecular compounds to investigate the ability to suppress the nonspecific adsorption onto the sensor chip surfaces. A sensorgram obtained by perfusing CGP74514 (50 µM) for 2 minutes and then Tween 20 (0.005 wt %) for 2 minutes into each sample is shown in FIG. 6.

CGP74514 and Tween 20 were nonspecifically adsorbed on the Sample 5, which was a commercially available CMD-bound surface, whereas the nonspecific adsorption of both CGP74514 and Tween 20 was hardly observed for the Samples 2 and 6. This demonstrated that a CMD-bound surface having more excellent ability to suppress the nonspecific adsorption of a low-molecular compound than that of a commercially available CMD-bound surface can be produced conveniently by the present approach.

Example B7

This Example relates to the production of sensor chips at varying concentrations of CMD for spin coating.
(1) Preparation of Sample 7 (Example)
Sample 7 was obtained by the same procedures as in the preparation of the Sample 3 except that a CMD concentration was changed to 0.2%.
(2) Preparation of Sample 8 (Example)
Sample 8 was obtained by the same procedures as in the preparation of the Sample 3 except that a CMD concentration was changed to 0.1%.
(3) Preparation of Sample 9 (Example)
Sample 9 was obtained by the same procedures as in the preparation of the Sample 3 except that a CMD concentration was changed to 0.08%.
(4) Preparation of Sample 10 (Example)
Sample 10 was obtained by the same procedures as in the preparation of the Sample 3 except that a CMD concentration was changed to 0.05%.
(5) Preparation of Sample 11 (Example)
Sample 11 was obtained by the same procedures as in the preparation of the Sample 3 except that a CMD concentration was changed to 0.02%.

Example B8

This Example relates to the preconcentration of a protein on the sensor chips obtained in Examples B1, B5, and B7. The preconcentration of BSA was investigated by totally the same procedures as in Example B2. The obtained results are summarized in Table 4.

TABLE 4

Preconcentration of BSA on CMD-bound surface

| Sample name | CMD concentration for spin coating | BSA pre-concentration | Remarks |
| --- | --- | --- | --- |
| Sample 5 | — | 22101 RU | Comparative Example |
| Sample 6 | — | 38892 RU | Comparative Example |
| Sample 2 | 0.5% | 72893 RU | Present invention |
| Sample 7 | 0.2% | 60105 RU | Present invention |
| Sample 8 | 0.1% | 43337 RU | Present invention |
| Sample 9 | 0.08% | 31765 RU | Present invention |
| Sample 10 | 0.05% | 18793 RU | Present invention |
| Sample 11 | 0.02% | 4356 RU | Present invention |

It was demonstrated that the amount of preconcentration of a protein can be controlled by controlling the concentration of an active esterified CMD solution for spin coating. It is considered that a higher concentration of an active esterified CMD solution from which a spin-coating thin film is obtained increases more the amount of CMD immobilized on a substrate surface, thereby resulting in an increased amount of preconcentration of a protein.

Example B9

This Example relates to the production of sensor chips at varying revolution speeds for spin coating.
(1) Preparation of Sample 12 (Example)
Sample 12 was obtained by the same procedures as in the preparation of the Sample 5 except that the revolution speed during spin coating was changed to 4000 rpm.
(2) Preparation of Sample 13 (Example)
Sample 13 was obtained by the same procedures as in the preparation of the Sample 5 except that the revolution speed during spin coating was changed to 1000 rpm.

Example B10

This Example relates to the preconcentration of a protein on the sensor chips obtained in Examples B1 and B9. The preconcentration of BSA was investigated by totally the same procedures as in Example B2. The obtained results are summarized in Table 5.

TABLE 5

Preconcentration of BSA on CMD-bound surface

| Sample name | The revolution speed during spin coating | BSA pre-concentration | Remarks |
| --- | --- | --- | --- |
| Sample 3 | 7000 rpm | 43337 RU | Present invention |
| Sample 12 | 4000 rpm | 51837 RU | Present invention |
| Sample 13 | 1000 rpm | 62239 RU | Present invention |

It was demonstrated that the amount of preconcentration of a protein can be controlled by controlling the revolution speed during spin coating. It is considered that a lower revolution speed at which a spin-coating thin film is obtained increases more the amount of CMD immobilized on a substrate surface, thereby resulting in an increased amount of preconcentration of a protein.

Example B11

A hydrogel film capable of immobilizing a protein thereon was produced by use of a highly water-soluble SAM compound to evaluate the amount of immobilization of a protein and nonspecific adsorption performance.
(1) Preparation of Substrate
A mixture aqueous solution (4.995 mM 6-hydroxy-1-undecanethiol/0.005 mM 8-amino-1-octanethiol, hydrochloride) of 6-hydroxy-1-undecanethiol (manufactured by Aldrich) and 8-amino-1-octanethiol, hydrochloride (manufactured by Dojindo Laboratories) was prepared. This solution was designated as Solution A. Next, a gold thin film was formed by a method described below on the upper surface of a plastic prism obtained by injection-molding ZEONEX (manufactured by Zeon Corp).

The prism was secured to a substrate holder of a sputtering apparatus, and a vacuum (base pressure of 1×10-3 Pa or less) was drawn therein. Thereafter, Ar gas was introduced (1 Pa) to the apparatus, and RF power (0.5 kW) was applied to the substrate holder for approximately 9 minutes with the substrate holder rotated (20 rpm) to plasma-treat the prism surface. Next, Ar gas was stopped, and a vacuum was drawn therein. Ar gas was introduced (0.5 Pa) again to the apparatus, and DC power (0.2 kW) was applied to a 8-inch Cr target for approximately 30 seconds with the substrate holder rotated (10 to 40 rpm) to draw a 2-nm Cr thin film thereon. Subsequently, Ar gas was stopped, and a vacuum was drawn again. Ar gas was introduced (0.5 Pa) again to the apparatus, and DC power (1 kW) was applied to a 8-inch Au target for approximately 50 seconds with the substrate holder rotated (20 rpm) to draw an approximately 50-nm Au thin film thereon.

The above-obtained sensor stick on which the Au thin film was drawn was dipped in the Solution A at 40° C. for 1 hour and washed ten times with ultrapure water.

(2) Active Esterification of CMD (Carboxymethyl Dextran)

After the dissolution of 4.95 ml of a solution of 0.1% by weight of CMD (manufactured by Meito Sangyo; molecular weight of 1,000,000), a mixture solution of EDC (0.4 M)/NHS (0.1 M) was added thereto in a calculation amount (50 µl) that activated 2% of the carboxyl groups through the reaction of the whole amount of the mixture solution, followed by stirring at room temperature.

(3) Binding Reaction of CMD to Substrate

Onto the substrate prepared in the paragraph (1), 500 µl of the active esterified CMD solution prepared in the paragraph (2) was added dropwise and spin-coated at 1000 rpm for 45 seconds to thereby form a thin film of the active esterified carboxymethyl dextran on the substrate having an amino group. After reaction at room temperature for 1 hour, the substrate was washed five times with 0.1 N NaOH and five times with ultrapure water to obtain Sample 1.

Example B12

Example B12 relates to the immobilization of a protein on the sensor sample obtained in Example B11. CA (carbonic anhydrase; manufactured by SIGMA) was used as the protein.

The Sample 1 prepared in Example B11 was loaded onto a surface plasmon resonance apparatus. A PBS buffer was injected thereto, and a base line was confirmed (the resonance angle here was used as a reference point). Then, the injection of an aqueous solution containing 0.2 M EDC (1-(3-dimethylaminopropyl)-3-ethylcarbodiimide) and 50 mM NHS (N-hydroxysuccinimide) and 7-minute standing, next the injection of a PBS buffer and 1-minute standing, next the injection of 0.1 mg/ml CA solution (acetic acid buffer, pH 5.0) and 15-minute standing, next the injection of a PBS buffer and 1-minute standing, next the injection of 1 M ethanol amine solution (Biacore) and 7-minute standing, next the injection of a PBS buffer and 1-minute standing, next three runs of the injection of 10 mM NaOH and 1-minute standing, and finally the injection of a PBS buffer and 1-minute standing were performed. The difference between the resonance angle here and the original resonance angle was used as the amount of CA immobilization. In this context, a resonance angle of 1/10000 degrees is referred to as 1 RU.

The amount of CA immobilization was 5200 RU. It was shown that a large amount of proteins can be immobilized even on a surface prepared with a highly water-soluble SAM compound.

Example B13

Example B13 relates to the nonspecific adsorption of a low-molecular compound on the sensor sample obtained in Example B11. CGP74514 as an inhibitor for cyclin-dependent kinases and Tween 20 as a surfactant were selected as the low-molecular compounds to investigate the ability to suppress the nonspecific adsorption onto the sensor sample surface.

The Sample 1 prepared in Example B11 was loaded onto a surface plasmon resonance apparatus. A PBS buffer was injected thereto, and a base line was confirmed (the resonance angle here was used as a reference point). Then, the injection of a PBS buffer solution of CGP74514 (50 µM) or a PBS buffer solution of Tween 20 (0.005% by weight) and 2-minute standing and finally the injection of a PBS buffer and 2-minute standing were performed. The difference between the resonance angle here and the original resonance angle was used as the amount of nonspecific adsorption.

The amounts of nonspecific adsorption on the Sample 1 were 3 RU (CGP74514) and 5 RU (Tween 20). It was shown that the nonspecific adsorption of a low-molecular compound can be suppressed even on a surface prepared with a highly water-soluble SAM compound.

Example C1

A hydrogel film capable of immobilizing a protein thereon was produced by use of a highly water-soluble SAM compound to evaluate the amount of immobilization of a protein and nonspecific adsorption performance.

(1) Preparation of Substrate 1 mM aqueous solution of 6-amino-1-octanethiol, hydrochloride (manufactured by Dojindo Laboratories) was prepared. This solution was designated as Solution A.

Next, a gold thin film was formed by a method described below on the upper surface of a plastic prism obtained by injection-molding ZEONEX (manufactured by Zeon Corp). The prism was secured to a substrate holder of a sputtering apparatus, and a vacuum (base pressure of 1×10-3 Pa or less) was drawn therein. Thereafter, Ar gas was introduced (1 Pa) to the apparatus, and RF power (0.5 kW) was applied to the substrate holder for approximately 9 minutes with the substrate holder rotated (20 rpm) to plasma-treat the prism surface. Next, Ar gas was stopped, and a vacuum was drawn therein. Ar gas was introduced (0.5 Pa) again to the apparatus, and DC power (0.2 kW) was applied to a 8-inch Cr target for approximately 30 seconds with the substrate holder rotated (10 to 40 rpm) to draw a 2-nm Cr thin film thereon. Subsequently, Ar gas was stopped, and a vacuum was drawn again. Ar gas was introduced (0.5 Pa) again to the apparatus, and DC power (1 kW) was applied to a 8-inch Au target for approximately 50 seconds with the substrate holder rotated (20 rpm) to draw an approximately 50-nm Au thin film thereon.

The above-obtained sensor stick on which the Au thin film was drawn was dipped in the Solution A at 40° C. for 1 hour and washed five times with ultrapure water.

(2) Activation of CMD (Carboxymethyl Dextran)

After the preparation of 10 g of a solution of 1% by weight of CMD (manufactured by Meito Sangyo; average molecular weight of 1,000,000; carboxymethyl group substitution degree per sugar unit: 0.65), 0.5 ml of 0.4 M aqueous solution of EDC (1-Ethyl-3-(3-dimethylaminopropyl)carbodiimide, hydrochloride) which is a carbodiimide derivative, and 9.5 ml of ultrapure water were added thereto, followed by stirring at room temperature for 5 minutes.

(3) Binding Reaction of CMD to Substrate

Onto the substrate prepared in the paragraph (1), 1 ml of the activated CMD solution prepared in the paragraph (2) was added dropwise and spin-coated at 1000 rpm for 45 seconds to thereby form a thin film of the active esterified carboxymethyl dextran on the substrate having an amino group. After reaction at room temperature for 15 minutes, the substrate was immersed in 1N NaOH for 30 minutes and was washed five times with ultrapure water to obtain Sample 1.

Example C2

By the same way as in Example B12, the sensor sample obtained in Example C1 was evaluated. The CA immobilization amount was 6300 RU.

Example C3

By the same way as in Example B13, the sensor sample obtained in Example C1 was evaluated. The amount of nonspecific adsorption was 2RU (CGP74514) and 4RU (Tween 20).

EFFECTS OF THE INVENTION

According to the present invention, a biosensor with a large amount of immobilization of a physiologically active substance and a small amount of nonspecific adsorption can be produced conveniently by use of a safe material.

The invention claimed is:

1. A method for producing a biosensor, which comprises:
   (i) active-esterifying a polysaccharide having a carboxyl group to obtain a polysaccharide having a carboxylic acid active ester group; and
   (ii) bringing into contact, by a spin coating method, the polysaccharide having a carboxylic acid active ester group with a substrate surface coated with an organic layer having a functional group, to thereby bind the polysaccharide having a carboxylic acid active ester group to the organic layer, wherein
   an aqueous solution, consisting essentially of water, and containing the polysaccharide having a carboxylic acid active ester group is coated on the substrate surface and water of the aqueous solution is evaporated to form a thin film of the polysaccharide having a carboxylic acid active ester group bound to the organic layer coated on the substrate surface,
   the organic layer having a functional group is a self-assembled monolayer or one or more alkanethiols, the self-assembled monolayer having an amino group, and
   the polysaccharide having a carboxylic acid active ester group is covalently bound to the organic layer on the substrate surface by a reaction between said amino group and said carboxylic acid active ester group.

2. The method according to claim 1, wherein the substrate surface coated with an organic layer having a functional group is a substrate surface coated with a mixture of alkanethiol having an amino group and alkanethiol having a hydrophilic group.

3. The method according to claim 2, wherein the hydrophilic group in the alkanethiol having a hydrophilic group is a hydroxyl group or oligoethylene glycol group.

4. The method according to claim 2, wherein the mixture of alkanethiol having an amino group and alkanethiol having a hydrophilic group comprises the alkanethiol having an amino group and the alkanethiol having a hydrophilic group at a molar ratio ranging from 1/1 to 1/1,000,000.

5. The method according to claim 2, wherein the alkanethiol having an amino group has a molecular length larger than that of the alkanethiol having a hydrophilic group.

6. The method according to claim 1, wherein the polysaccharide having a carboxyl group is a carboxymethyl dextran.

7. The method according to claim 6, wherein the polysaccharide having a carboxylic acid active ester group is brought into contact with the substrate surface by a spin coating method to form the thin film of the polysaccharide having a carboxylic acid active ester group.

8. The method according to claim 1, wherein the polysaccharide having a carboxyl group is active-esterified with EDC and NHS, or with EDC alone in Step (i).

* * * * *